United States Patent
Alapuranen et al.

(10) Patent No.: US 7,361,487 B2
(45) Date of Patent: Apr. 22, 2008

(54) ENZYME FUSION PROTEINS AND THEIR USE

(75) Inventors: Marika Alapuranen, Rajamäki (FI); Leena Valtakari, Rajamäki (FI); Jarno Kallio, Järvenpää (FI); Pentti Ojapalo, Tuusula (FI); Jari Vehmaanperä, Klaukkala (FI)

(73) Assignee: AB Enzymes Oy, Rajamaki (FI)

( * ) Notice: Subject to any disclaimer, the term of this patent is extended or adjusted under 35 U.S.C. 154(b) by 0 days.

(21) Appl. No.: 11/404,065

(22) Filed: Apr. 13, 2006

(65) Prior Publication Data

US 2007/0244020 A1 Oct. 18, 2007

(51) Int. Cl.
| | |
|---|---|
| C12P 21/04 | (2006.01) |
| C12N 9/42 | (2006.01) |
| C12N 1/20 | (2006.01) |
| C12N 1/00 | (2006.01) |
| A23K 1/00 | (2006.01) |
| C11D 3/386 | (2006.01) |
| C07H 21/04 | (2006.01) |

(52) U.S. Cl. ............... 435/69.7; 435/209; 435/252.33; 435/254.1; 435/484; 426/635; 510/320; 536/23.2; 536/23.4

(58) Field of Classification Search ............ None
See application file for complete search history.

(56) References Cited

U.S. PATENT DOCUMENTS

| | | | |
|---|---|---|---|
| 5,457,046 A | 10/1995 | Wöldike et al. | 435/209 |
| 5,770,418 A | 6/1998 | Yaver et al. | 435/189 |
| 5,843,745 A | 12/1998 | Berka et al. | 435/189 |
| 5,874,293 A | 2/1999 | Miettinen-Oinonen et al. | 435/263 |
| 5,916,799 A | 6/1999 | Foody et al. | 435/263 |
| 5,958,082 A | 9/1999 | Lund | 8/102 |
| 6,001,639 A | 12/1999 | Schülein et al. | 435/263 |
| 2004/0197890 A1* | 10/2004 | Lange et al. | 435/209 |
| 2006/0057672 A1* | 3/2006 | Bower et al. | 435/69.1 |

FOREIGN PATENT DOCUMENTS

| | | |
|---|---|---|
| EP | 0 244 234 | 11/1987 |
| EP | 0843041 | 5/1998 |
| WO | WO 94/07983 | 4/1994 |
| WO | WO 95/33386 | 12/1995 |
| WO | WO 96/23928 | 8/1996 |
| WO | WO 96/29397 | 9/1996 |
| WO | WO 97/08325 | 3/1997 |
| WO | WO 97/09410 | 3/1997 |
| WO | WO 97/14804 | 4/1997 |
| WO | WO 99/57260 | 11/1999 |
| WO | WO 01/70998 | 9/2001 |
| WO | WO 03/062409 | 7/2003 |
| WO | WO 03/000941 | 3/2005 |

OTHER PUBLICATIONS

Hong et al., Cloning of a gene encoding a thermo-stable endo-b-1,4-glucanase from *Thermoascus aurantiacus* and its expression in yeast. Biotechnol: Lett., 2003, vol. 25 : 657-661.*
Dabrowski et al, "Cloning and sequence analysis of the cellulose gene (cbh 1) encoding cellobuohydrolase . . . ," Database EMBL-EB1, accession No. Q69212, (2004).
Kim et al., "Functional Analysis of a Hybrid Endoglucanase of Bacterial Origin Having a Cellulose Binding Domain from a Fungal Exoglucanase," *Appld. Biochem. and Biotech.*, 75"193-204 (1998).
Leggio and Larsen, "The 1.62 Å structure of *Thermoascus aurantiacus* endoglucanase: . . . ," *FEBS Letters*, 523:103-108 (2002).
Liu et al., "Molecular cloning and sequence analysis of the cellulose gene . . . ," Database EMBL-EB1, accession No. Q5G2D5 (2005).
van den Hombergh et al., "Talaromyces emersonii beta-glucanase" Sequence 2 from WO 01/70998.
Altschul et al., "Basic Local Alignment Search Tool," *J. Mol. Biol.*, 215:403-410 (1990).
Bailey and Nevalainen, "Induction, isolation and testing of stable *Trichoderma reesei* mutants with improved production of solubilizing cellulose," *Enzyme Microb. Technol.*, 3:153-157 (1981).
Bendtsen et al., "Improved Prediction of Signal Peptides: SignalP 3.0," *J. Mol. Biol.*, 340:783-795 (2004).
Gasteiger et al., "ExPASy: the proteomics server for in-depth protein knowledge and analysis," *Nucleic Acids Research*, 31:3784-3788 (2003).
Ghose, "Measurement of cellulose activities," *Pure and Applied Chem.*, 590:257-268 (1987).
Haakana et al., "Cloning of cellulose genes from *Melanocarpus albomyces* and their efficient expression in *Trichoderma reesei*," *Enz. Microbiol. Technol.*, 34:159-167 (2004).
Henrissat, "A classification of glycosyl hydrolases based on amino acid sequence similarities," *Biochem. J.*, 280:309-316 (1991).
Henrissat and Bairoch "New families in the classification of glycosyl hydrolases based on amino acid sequence similarities," *Biochem J.*, 293:781-788 (1993).
Henrissat and Bairoch "Updating the sequence-based classification of glycosyl hydrolases," *Biochem J.*, 316:695-696 (1996).

(Continued)

*Primary Examiner*—Rebecca Prouty
*Assistant Examiner*—Ganapathirama Raghu
(74) *Attorney, Agent, or Firm*—Banner & Witcoff, Ltd.

(57) ABSTRACT

Cellulase fusion proteins comprising an endoglucanase core region and a heterologous cellulose binding domain are described. The fusion proteins may be produced by recombinant techniques using appropriate polynucleotides, expressing vectors and host cells. The fusion proteins and enzyme preparations thereof are useful in treating cellulosic material, such as textile material, and they are particularly useful in biostoning denim or in biofinishing fabrics and garments. In addition the fusion proteins may be used in pulp and paper industry, oil extraction from plants, detergent compositions, or for improving the quality of animal feed.

22 Claims, 5 Drawing Sheets

OTHER PUBLICATIONS

Hong et al, "Cloning of a gene encoding a thermo-stabile endo-β-1,4-glucanase from *Thermoascus aurantiacus* and its expression in yeast," *Biotech. Letters*, 25:657-661 (2003).

Joutsjoki et al., "Transformation of *Trichoderma reesei* with the *Hormoconis resinae* glucoamylase P (*gamP*) gene: production of a heterologous glucoamylase by *Trichoderma reesei*," *Curr. Genet.*, 24:223-228 (1993).

Karhunen et al., "High frequency one-step gene replacement in *Trichoderma reesei*. I. Endoglucanse I overproduction," *Mol. Gen. Genet.*, 241:515-522 (1993).

Malardier et al., "Cloning of the nitrate reductase gene (niaD) of *Aspergillus nidulans* and its use for transformation of *Fusarium oxysporum*," *Gene*, 78:147-156 (1989).

Needleman and Wunsch, "A General Method Applicable to the Search for Similarities in the Amino Acid Sequence of Two Proteins," *Journal of Molecular Biology*, 48:443-453 (1970).

Nielsen et al., "Identification of prokaryotic and eukaryotic signal peptides and prediction of their cleavage sites," *Protein Engineering*, 10(1):1-6 (1997).

Paloheimo et al., "High-Yield Production of a Bacterial Xylanase in the Filamentous Fungus *Trichoderma reesei* Requires a Carrier Polypeptide with an Intact Domain Structure," *Appl. Env. Microbiol.* 69(12):7073-7082 (2003).

Penttilä et al., "A versatile transformation system for the cellulolytic filamentous fungus *Trichoderma reesei*," *Gene*, 61:155-164 (1987).

Raeder and Broda, "Rapid preparation of DNA from filamentous fungi," *Lett. Appl. Microbiol.*, 1:17-20 (1985).

Rice et al., "EMBOSS: The European Molecular Biology Open Software Suite," *Trends in Genetics*, 16(6):276-277 (2000).

Srisodsuk et al., "Role of the Interdomain Linker Peptide of *Trichoderma reesei* Cellobiohydrolase I in Its Interaction with Crystalline Cellulose," *J. Biol. Chem.*, 268(28):20756-20761 (1993).

Stålbrand et al., "Purification and characterization of two β-mannanases from *Trichodermra reesei*," *J. Biotechnol.*, 29:229-242 (1993).

Ward et al., "Cloning, Sequence and Preliminary Structural Analysis of a Small, High pL Endoglucanase (EGIII) from *Trichoderma reesei*" Eds. Soumincn and Reinikainen, *Proceedings of the second TRICEL symposium on Trichoderma reesei Cellulases and Other Hydrolases*, Espoo, Finland; Foundation for Biotchenical and Industrial Fermentation Research, 8:153-158 (1993).

English abstract of WO 95/33386.

Dabrowski et al., "Cloning, expression and purification of CBHI exoglucanase from *Chaetomium thermophilum* DSM1495," *EMBL-EBI*, Accession No. Q69212 (2004).

Ito et al., "Improvement of Cellulose-Degrading Ability of a Yeast Strain Displaying *Trichoderma resei* Endoglucanase II by Recombination of Cellulose-Binding Domains," *Biotechnol.*, 29:688-691 (2004).

Li et al., "Purification and characterization of a cellobiohydrolase from the thermophilic fungus Chaetomium thermophilum CTW," *Weishengwu Xuebao*, 46(1):143-146 (2006) (abstract) Epoquenet Biosis., Accession No. PREV200600253839.

* cited by examiner

ENZYME FUSION PROTEINS AND THEIR USE

FIELD OF THE INVENTION

The present invention relates to enzyme technology, and more precisely to cellulase fusion proteins comprising a catalytic domain and a cellulose binding domain. The fusion proteins may be produced by recombinant techniques using appropriate polynucleotides, expressing vectors and host cells, which are also encompassed by the invention. The fusion proteins and enzyme preparations thereof are useful in treating cellulosic material, such as textile material. In addition the fusion proteins may be used in pulp and paper industry, oil extraction from plants, detergent compositions, or for improving the quality of animal feed. The invention thus further relates to a process for treating cellulosic material with the fusion protein, and especially to processes for biostoning or biofinishing fabrics or garments, especially denim. The invention still further relates to detergent compositions and animal feed containing the fusion proteins.

BACKGROUND OF THE INVENTION

Cellulose is the major structural component of higher plants and occurs naturally in almost pure form only in cotton fiber. It provides plant cells with high tensile strength helping them to resist mechanical stress and osmotic pressure. Cellulose is a linear polysaccharide of glucose residues connected by β-1,4-linkages. In nature cellulose is usually associated with lignin and hemicelluloses. Cellulosic material is degraded in nature by a number of various organisms including bacteria and fungi. The biological conversion of cellulose to glucose generally requires three major groups of enzymes: cellobiohydrolases (CBH), endoglucanases (EG) and beta-glucosidases (BG).

There is a wide spectrum of industrial applications of cellulases. In the textile industry, cellulases are used in denim finishing to create a fashionable stone washed appearance in denim cloths in a biostoning process. Cellulases are also used, for instance, to clean fuzz and prevent formation of pills on the surface of cotton garments. In detergent industry cellulases are used to brighten colors and to prevent graying and pilling of garments. Cellulases are further used in food industry and animal feed manufacturing, and they have a great potential in the pulp and paper industry, for instance, in deinking to release ink from fiber surfaces and in improving pulp drainage.

Industrially used cellulases are often mixtures of enzymes having a variety of activities and substrate specificities. The commercial enzyme preparations often comprise all three cellulase activities i.e. CBH, EG and BG. In addition the unique properties of each cellulase make some more suitable for certain purposes than others, and therefore efforts have also been made to obtain and use cellulases having only the desired activities. The most widely used cellulases of fungal origin are derived from *Trichoderma reesei*. However, also other fungal sources have been suggested e.g., in U.S. Pat. No. 5,457,046.

Cellulases applied in denim treatment are usually divided into two main groups: acid and neutral cellulases. Acid cellulases typically operate at pH 4.0 to 5.5 and neutral cellulases in the range of pH 6 to 8. Cellulases having characteristics of both the acid and neutral group can be called hybrid cellulases. Acid cellulases used in biostoning mainly originate from *Trichoderma reesei* (sexual form *Hypocrea jecorina*) and the neutral cellulases come from a variety of fungi, including genera of *Melanocarpus*, *Humicola*, *Myceliophthora*, *Fusarium*, *Acremonium*, and *Chrysosporium* (Haakana et al. 2004). *T. reesei* enzymes include, e.g., cellulases from the glycosyl hydrolase family 5 (endoglucanase II, EGII), family 7 (cellobiohydrolase 1, CBHI) and family 12 (endoglucanase III, EGIII; Ward et al. 1993), and the neutral cellulases, most often endoglucanases, from family 45 and family 7 (Henrissat, 1991; Henrissat and Bairoch, 1993, 1996).

U.S. Pat. No. 5,874,293 discloses an improved cellulase composition comprising elevated amounts of EGII endoglucanase of *T. reesei* for treating cellulose-containing textiles. The composition improved color properties, increased lightness and visual appearance and reduced pilling tendencies. WO97/14804 discloses one 20 kDa and one 50 kDa cellulase with endoglucanase activity derived from *Melanocarpus* sp. that are especially useful in the textile and detergent industry. Fusion proteins containing the 20K- or 50K-proteins linked to a cellulose binding domain preferably from *Trichoderma reesei* are suggested for creating new enzyme properties. No specific examples are given, nor are the desired properties described.

However, there is still a need for improved cellulases, including endoglucanases that are more efficient in fabric treatment and in other fields, where cellulases traditionally are used. In particular, there is a continuous need for more efficient cellulases to improve the process economics. The present invention aims to meet these needs.

In textile industry a "stone washed" look or an abraded look has been denim producers' interest in recent years. Traditional stone washing with pumice stones reduces the strength of fabric and burdens the laundering apparatuses. There is a trend towards enzymatic denim finishing processes, and cellulases have replaced or are being used together with pumice stones to give the fabric its desired "worn" look. Controlled enzyme treatments result in less damage to the garments and machines and eliminate the need for disposal of stones.

A general problem associated with enzymatic stone washing is backstaining caused by redeposition of removed Indigo dye during or after abrasion. The repositioning of Indigo dye reduces the desired contrast between the white and indigo dyed yarns and it can be most easily noted on the reverse side of denim and the interior pockets (as increased blueness). On the face side this may be seen as reduced contrast between dyed areas and areas from which dye has been removed during biostoning. Backstaining can be reduced by using antibackstaining agents such as nonionic ethoxylated alcohols during the treatment or adding bleaching agents during rinsing steps. The nature of the enzyme has an impact on backstaining. Generally neutral cellulases backstain less than acid cellulases.

WO97/09410 describes that the addition of a certain type of cellulase to another cellulase having abrading activity reduces backstaining. The additional cellulase belongs to family 5 or 7, but it has no significant abrading effect in itself. Preferably said additional cellulase originates from *Bacillus* or *Clostridium*.

U.S. Pat. No. 5,916,799 discloses cellulase compositions containing both cellobiohydrolases and endoglucanases that have been subjected to limited proteolysis to separate the core and binding domains of the enzymes. The obtained enzyme compositions were found to reduce backstaining. WO 94/07983 relates to the finding that redeposition of colorant onto fabric during the stone washing process can be reduced by employing a fungal cellulase composition, which is substantially free of cellobiohydrolase type components.

WO96/23928 discloses treatment of cellulose containing fabrics with truncated cellulase enzymes. The truncated enzymes lacking cellulose binding domain (CBD) were found to reduce redeposition of dye and increase abrasion.

The general conclusion of the three references cited above could be that the cellulose binding domain has a negative effect on backstaining. However, the present invention now provides a cellulase construction with low backstaining property, despite the presence of a cellulose binding domain.

SUMMARY OF THE INVENTION

The present invention is based on the surprising finding that the effect of endoglucanses could be significantly enhanced by coupling thereto a particular cellulose binding domain without impairing the backstaining properties.

One object of the present invention is to provide novel endoglucanase fusion proteins having improved hydrolytic properties for use in textile industry, especially in stone washing denim. The fusion proteins of the invention have the advantage of being active at both acid and neutral pH values, and they have highly improved performance in biostoning applications. When used in treating denim, the fusion proteins provide a low backstaining effect. With the improved efficiency of the endoglucanases of the invention, the use of the enzymes is significantly more economical. Additional advantages are achieved also in terms of logistics and the storage of the enzyme products, because smaller amounts of the enzyme product are needed. The fusion proteins are also useful in detergent compositions, as well as in other fields such as feed industry, oil extraction from plants, or pulp and paper industry.

A further object of the present invention is to provide polynucleotides encoding the novel endoglucanase fusion proteins.

A still further object of the present invention is to provide a method for producing the fusion proteins.

A still further object of the present invention is to provide novel expression vectors containing such polynucleotides, useful for the production of the endoglucanase fusion proteins, as well as novel hosts transformed with said expression vectors.

A still further object of the present invention is to provide enzyme preparations, which contain one or more novel endoglucanase fusion proteins.

A still further object of the present invention is to provide methods of treating cellulosic material with the fusion protein e.g., for use in textile, detergent, animal feed, oil extraction from plants, or pulp and paper industry, and particularly for finishing of textiles, especially for biostoning and biofinishing of denim.

A still further object of the present invention is to provide animal feed or detergent compositions containing the fusion proteins.

The present invention relates to a cellulase fusion protein comprising a first amino acid sequence of an endoglucanase core, and a second amino acid sequence comprising a linker and cellulose binding domain (CBD) having at least 75% identity to SEQ ID NO: 15, or a variant or fragment thereof having cellulose binding activity.

The invention is further directed to an isolated polynucleotide selected from the group consisting of:
a) a nucleotide sequence of SEQ ID NO: 3 or 5, or a sequence encoding a cellulase fusion protein of claim 1,
b) a complementary strand of a),
c) a sequence that is degenerate as a result of the genetic code to anyone of the sequences of a) or b).

The invention still further relates to an expression vector comprising said nucleotide sequence, and to a host cell comprising the expression vector, as well as to an enzyme preparation comprising the fusion protein.

The invention also encompasses a method of producing the fusion protein, comprising the steps of transforming a host cell with an expression vector encoding said fusion protein and culturing said host cell under conditions enabling expression of said fusion protein, and optionally recovering and purifying the fusion protein produced.

The invention still further encompasses a process for treating cellulosic material, wherein said process comprises contacting the cellulosic material with the fusion protein.

The invention is also directed to a process for biostoning, which process comprises the step of contacting the cellulase fusion protein or the enzyme preparation with denim fabric or garments, and to a process for biofinishing, which comprises the step of contacting the cellulase fusion protein or the enzyme preparation with textile materials like fabrics or garments or yarn.

Eventually the invention is directed to a detergent composition comprising the fusion protein and detergent auxiliaries, to animal feed comprising the fusion protein, and to an *Eschrichia coli* strain having accession number *E. coli* DSM 18159.

Specific embodiments of the invention are set forth in the dependent claims.

Other objects, details and advantages of the present invention will become apparent from the following drawings, detailed description and examples.

DETAILED DESCRIPTION OF THE INVENTION

Figure 1:
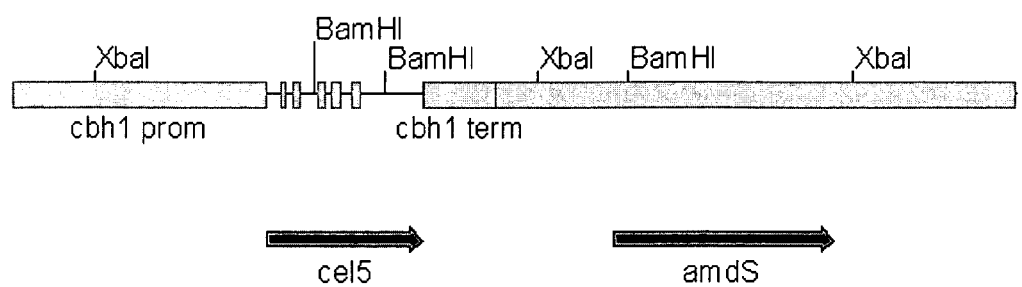
FIG. 1 illustrates a schematic picture of the expression cassette used in transformation of *T reesei* protoplasts for production of *T. aurantiacus* EG28 or EG28+CtCBD cellulase. The cel5A or cel5A_Ct cel7AlinkerCBD gene is under control of *T. reesei* cbhI promoter (cbhI prom) and transcription termination is ensured with the addition of the cbhI terminator (cbhI term). The amdS gene (amdS) is included for selection of transformants. The expression cassette for EG28 and EG28+CtCBD production was isolated as a 8.6 kb NotI fragment from pALK1930 or as a 8.9 kb NotI fragment from pALK1948, respectively.

Cellulases comprise a catalytic domain/core (CD) expressing cellulase activity. In addition to the catalytic domain the cellulase molecule may comprise one or more "cellulose binding domains" ("CBDs"), also named as carbohydrate binding domains/modules (CBD/CBM), which can be located either at the N- or C-terminus of the catalytic domain. CBDs have carbohydrate-binding activity and they mediate the binding of the cellulase to crystalline cellulose but have little or no effect on hydrolytic activity of the enzyme on soluble substrates. These two domains are typically connected via a flexible and highly glycosylated linker region, herein called "linker." Such constructs are described e.g., in Srisodsuk et al., 1993. Some of the naturally occurring endoglucanases and cellobiohydrolases have a cellulose binding domain (CBD), while others do not.

Endoglucanases (EGs) are one of the three types of cellulases generally needed for the biological conversion of cellulose to glucose. Endoglucanases cut internal beta-1,4-glucosidic bonds, whereas cellobiohydrolases cut the disaccharide cellobiose from the end of the cellulose polymer chain and beta-1,4-glucosidases hydrolyze the cellobiose and other short cello-oligosaccharides to glucose. "Endoglucanase" ("EG") in connection with the present invention refers to enzymes classified as E.C. 3.2.1.4. They are 1,4-beta-D-glucan 4-glucanohydrolases and catalyze endohydrolysis of 1,4-beta-D-glycosidic linkages in polymers of glucose such as cellulose. Some endoglucanases may also hydrolyse e.g., 1,4-linkages in beta-D-glucans also containing 1,3-linkages. They may therefore also be classified as endo-1,3(4)-beta-glucanases (E.C. 3.2.1.6). Thus, an enzyme may catalyze reactions on several substrates and can belong to multiple classes.

Cellulases including endoglucanases can also be classified into various glycosyl hydrolase families according their primary sequence, supported by analysis of the three dimensional structure of some members of the family (Henrissat 1991, Henrissat and Bairoch 1993, 1996). For example family 45 (formerly celK) contains endoglucanases (EC 3.2.1.4), and family 5 (formerly known as celA) consists mainly of endoglucanases (EC 3.2.1.4). Family 7 (formerly cellulase family celC) contains both endoglucanases and cellobiohydrolases. Some glycosyl hydrolases are multifunctional enzymes that contain catalytic domains that belong to different glycosyl hydrolase families. For the present purposes the endoglucanase part of the fusion protein preferably belongs to the glycoside hydrolase family 45 or family 5, and more preferably to family 5.

According to a preferred embodiment of the invention the endoglucanase part of the fusion protein is derived from a fungus, preferably of the genus *Thermoascus*, and more preferably from *Thermoascus aurantiacus*. Such an endoglucanase has been described e.g., by Hong et al. 2003. WO 03/062409 suggests using this enzyme for feed applications, because in addition to endoglucanase it also has beta-glucanase activity. Most preferably the endoglucanase is derived from *T. aurantiacus* strain ALK04242 deposited as CBS116239. The endoglucanase gene of said strain has been inserted into plasmid pALK1926 and deposited as DSM 17326. The protein encoded by this gene is herein referred to as "Ta EG28" or simply "EG28".

Alternatively, the endoglucanase part of the fusion protein may be obtained from *Acremonium* sp. preferably from *A. thermophilum*, and more preferably from a strain having the characteristics of the strain ALK04245 deposited as CBS116240. The endoglucanase obtainable from this strain and encoded by the gene cel45A is herein referred to as "At EG40" or simply "EG40".

Endoglucanase "core" as used herein, means the catalytic domain/core (CD) of an enzyme expressing at least endoglucanase activity. Such a catalytic domain may be in its naturally occurring form (i.e., intact) or, it may be modified.

According to one embodiment of the invention, the endoglucanase core has at least 75, 80, 85, 90, 95, 98 or 99% identity to SEQ ID NO: 2 (Ta EG28). Preferably, the core comprises at least the mature protein, which corresponds to amino acids 19 to 334 of SEQ ID NO: 2. The prediction on the signal sequence was made using the program SignalP V3.0 (Nielsen et al., 1997; Bendtsen et al., 2004); the NN value was obtained using neural networks and HMM value using hidden Markov models. Alternatively the endoglucanase part of the fusion protein has at least 75, 80, 85, 90, 95, 98 or 99% identity to the endoglucanase core of At EG40, encoded by a polynucleotide comprised in SEQ ID NO: 8. Preferably, the core comprises at least the mature protein, which corresponds to amino acids 22 to 297 of EG40.

"Cellobiohydrolase" or "CBH" as used herein refers to enzymes that cleave cellulose from the end of the glucose chain and produce mainly cellobiose. They are also called 1,4-beta-D-glucan cellobiohydrolases or cellulose 1,4-beta-cellobiosidases. They hydrolyze the 1,4-beta-D-glucosidic linkages from the reducing or non-reducing ends of a polymer containing said linkages, such as cellulose, whereby cellobiose is released.

The CBD including the linker is preferably derived from *Chaetomium thermophilum*, and especially from the cellobiohydrolase (CBHI/Cel7A) encoding gene of strain ALKO4265, deposited as CBS 730.95. This CBD including the linker is referred to as "CtCBD". According to a preferred embodiment of the invention, the linker plus the cellulose binding domain has a sequence that has at least 80, 85, 90, 95, 98 or 99% identity to SEQ ID NO: 15, (which corresponds to amino acids 335-415 of SEQ ID NO: 4). According to another preferred embodiment, the second amino acid sequence comprises amino acids 335-379 of SEQ ID NO: 4.

The term "derived from," in connection with a microorganism source, means that the polypeptide may naturally be produced by said specific microorganism source, or the polynucleotide encoding the polypeptide may be isolated from said microorganism source, or the term means a host cell into which the polynucleotide from said microorganism source encoding the polypeptide has been introduced. However it does not exclude minor modifications of the sequence e.g., by substitution, deletion, inversion and/or insertion of one or a few amino acids/codons as long as the biological activity of the encoded protein is retained.

The core, and the linker+CBD, respectively, may also be a fragment or a variant of said sequences, wherein said fragment or variant has cellulase activity and/or cellulose binding activity. For example the first amino acid sequence may comprise a fragment or variant of an amino acid sequence having at least 75% identity to SEQ ID NO: 2 or 8, and the second amino acid sequence may comprise a fragment or variant of an amino acid sequence having at least 75% identity to SEQ ID NO: 15.

In the present context, "cellulase activity" means catalytic ability to hydrolyse cellulose or derivatives thereof, such as endoglucanase or beta-glucanase activity. In addition to endoglucanase and/or beta-glucanase activity, some of the cellulases may further have hemicellulase and/or xylanase activity.

As used in the present context the term "identity" refers to the global identity between two amino acid sequences compared to each other from the first amino acid encoded by the corresponding gene to the last amino acid. The identity of the full-length sequences is measured by using Needleman-Wunsch global alignment program at EMBOSS (European Molecular Biology Open Software Suite; Rice et al., 2000) program package, version 3.0.0, with the following parameters: EMBLOSUM62, Gap penalty 10.0, Extend penalty 0.5. The algorithm is described in Needleman and Wunsch (1970). The man skilled in the art is aware of the fact that results using Needleman-Wunsch algorithm are comparative only when aligning corresponding domains of the sequence. Consequently comparison of e.g., cellulase sequences including CBD or signal sequences with sequences lacking those elements are excluded as not being meaningful.

According to one embodiment of the invention, the fusion protein contains an endoglucanase core encoded by a gene equivalent to that included in *E. coli* DSM 17326. Preferably, the fusion protein is encoded by a fusion gene equivalent to that included in *E. coli* DSM 18159. According to a specific embodiment of the invention the fusion protein contains an endoglucanase core comprising the sequence of SEQ ID NO:2 and a linker and CBD comprising the sequence of SEQ ID NO: 15. Especially it comprises the amino acid sequence of SEQ ID NO: 4 or 6, or a variant or fragment thereof having cellulase and cellulose binding activity.

A "fragment" is understood to be part of a specific amino acid sequence that is long enough to have the desired biological activity. In other words, the fragment may be e.g., only the mature part of the amino acid sequence or even a subsequence of the mature part. By an amino acid sequence that is a "variant" of a specific amino acid sequence is meant an amino acid sequence that is not identical to the specific amino acid sequence, but rather contains at least some amino acid changes i.e. deletions, substitutions, inversions, insertions etc. that do not essentially affect the biological activity of the protein as compared to a similar activity of the specific amino acid sequence, when used for the desired purpose. Biological activity in this context thus refers to cellulase activity, cellulose binding activity or both.

The fusion protein of the invention may be prepared by attaching the endoglucanase core part to the linker and CBD part in the appropriate encoding DNA using generally known recombinant DNA techniques. Briefly the polynucleotides encoding the fusion partners are amplified and cloned, nucleotides may also be synthetized. The fused polynucleotide is inserted into an expression vector, transformed into a host cell and expressed. Preferably the linker and CBD is attached at the C-terminus of the endoglucanase core.

An "expression vector" is a cloning plasmid or vector capable of expressing DNA encoding the endoglucanase fusion proteins after transformation into a desired host. When a fungal host is used, the gene of interest is preferably provided to a fungal host as part of a cloning or expression vehicle that integrates into the fungal chromosome, or allows the gene of interest to integrate into the host chromosome. Other sequences that are part of the cloning vehicle or expression vehicle may also be integrated with said DNA during the integration process. In addition, in fungi the expression vector or parts thereof can be targeted into predetermined loci. Alternatively, the desired fusion gene is provided as an autonomously replicating plasmid.

The DNA encoding the endoglucanase fusion proteins is preferably placed under the control of (i.e., operably linked to) certain control sequences such as promoter sequences provided by the vector. Upon transformation these control sequences integrate into the host genome with the gene of interest. Alternatively, the control sequences can be those at the integration site.

The expression control sequences of an expression vector will vary depending on whether the vector is designed to express a certain gene in a prokaryotic or in a eukaryotic host (for example, a shuttle vector may provide a gene for selection in bacterial hosts). Expression control sequences can contain transcriptional regulatory elements such as promoters, enhancer elements, and transcriptional termination sequences, and/or translational regulatory elements, such as translational initiation and termination sites.

A polynucleotide molecule, such as DNA, is said to be capable of expressing a polypeptide, if it contains expression control sequences, which contain transcriptional regulatory information and such sequences are operably linked to the nucleotide sequence, which encodes the polypeptide.

An operable linkage is a linkage in which a sequence is connected to a regulatory sequence (or sequences) in such a way as to place expression of the sequence under the influence or control of the regulatory sequence. Two DNA sequences (such as a promoter region sequence linked to the 5' end of the protein encoding sequence) are said to be operably linked if function of promoter results in the transcription.

The vectors of the invention may further comprise other operably linked regulatory elements, such as enhancer sequences.

In a preferred embodiment, genetically stable transformants are constructed, whereby the DNA encoding the fusion proteins is integrated into the host chromosome by transformation with a vector, which may harbor sequences promoting integration of said vector into the chromosome.

Cells that have stably integrated DNA encoding the endoglucanase fusion proteins into their chromosomes may be selected e.g., by introduced marker(s), homologous or heterologous, which allow for selection of host cells which contain the expression vector in the chromosome, for example the marker may provide biocide resistance, e.g., resistance to antibiotics, or heavy metals, such as copper, or markers complementing an auxotrophic mutation in the host chromosome, and the like. The selectable marker can for example be a selection gene directly linked to the DNA gene sequences to be expressed, or introduced into the same cell by co-transformation. Also other selection systems can be used.

Once the expression vector containing the DNA encoding the fusion protein is prepared, it is introduced into an appropriate host cell by any of a variety of suitable means, including transformation as known in the art. After transformation, recipient cells are grown in an appropriate selective medium, which selects for the growth of transformed cells.

Suitable expression and production host systems are for example the production system developed for fungal hosts *Trichoderma* (EP 244 234), or *Aspergillus*, such as *A. oryzae* or *A. niger* (WO 97/08325 and WO 95/33386, U.S. Pat. No. 5,843,745, U.S. Pat. No. 5,770,418), or the production system developed for *Fusarium*, such as *F. oxysporum* (Malardier et al., 1989). Suitable production systems developed for bacteria include a production system developed for

*Bacillus*, for example *B. subtilis, B. licheniformis, B. amyloliquefaciens* or for *E. coli* or for an actinomycete *Streptomyces*. Suitable production systems developed for yeasts are systems developed for *Saccharomyces, Shizosaccharomyces* or *Pichia pastoris*. Production systems in other microbes or in mammalian cells or in plants are also possible.

Expression of the cloned gene sequence(s) results in the production of the desired protein, or in the production of a fragment of this protein. This expression can take place in a continuous manner in the transformed cells, or in a controlled manner.

To obtain the enzyme preparations of the invention, the hosts having the desired properties (that is, hosts capable of expressing economically feasible quantities of the endoglucanase fusion proteins) are cultivated under suitable conditions, and the desired enzymes are preferably secreted from the hosts into the culture medium, and optionally recovered from said culture medium by methods known in the art. Preferably, the host for such production is a filamentous fungus, such as *Trichoderma* or *Aspergillus*, and especially *T. reesei*.

As used in the present context, the "enzyme preparation" refers to any enzyme product, which contains at least one endoglucanase fusion protein of the invention. Thus, such an enzyme preparation may be a spent culture medium or filtrate. Spent culture medium means the culture medium of the host comprising the produced enzymes. Preferably, the host cells are separated from said medium after the production. If desired, such preparations may be lyophilized or the enzymatic activity otherwise concentrated and/or stabilized for storage. If required, a desired enzyme may be further purified in accordance with conventional methods, such as extraction, precipitation, chromatography, affinity chromatography, electrophoresis, or the like.

However, it is an advantage of the invention that the culture medium with or without host cells may be utilized as an enzyme preparation as such without further purification, because the endoglucanase fusion proteins can be secreted into the culture medium, and they display activity in the ambient conditions of the spent culture medium. The enzyme preparations are very economical to provide and use, because isolation of a specific enzyme from the culture medium is unnecessary.

In addition to the endoglucanase fusion protein, the enzyme preparations may comprise one or more other enzymes, which may be for example other cellulases, amylases, lipases, proteases, hemicellulases, xylanases, pectinases and/or oxidases such as laccases and peroxidases. Alternatively, before, during or after the treatment with the endoglucanase fusion protein another enzyme treatment may be carried out. The enzyme treatment may comprise, for example, one or more amylase treatments (e.g., for desizing of denim), one or more cellulase treatments and/or one or more peroxidase and/or laccase treatments. It depends on the application what other enzymes are included in the enzyme preparation or used in the enzyme treatment.

In addition to the fusion protein, the enzyme preparation may contain additives, such as stabilizers, buffers, preservatives, surfactants and/or culture medium components. Preferred additives are such, which are commonly used in enzyme preparations intended for the application, where the enzyme preparation is used.

The enzyme preparations may be provided as a liquid or as a solid, for example, as a dried powder or granular, especially non-dusting granules, or a stabilized liquid. It is envisioned that the enzyme preparations can be further enriched, or made partially or completely deficient in specific enzymatic activities, so as to satisfy the requirements of a specific utility in various applications e.g., in the textile industry. A mixture of enzyme activities secreted by a host—can be advantageous in a particular industrial application, for example in biofinishing and biostoning.

The endoglucanase fusion proteins and the preparations thereof are useful e.g., in textile, feed, plant oil, detergent, and pulp and paper industry. They may be used for treating any cellulosic material, such as textile material, plants used in animal feed, plant material for oil extraction, or wood-derived mechanical or chemical pulp or secondary fiber. They may also be added into detergents, which normally contain auxiliaries, such as surface-active agents, surfactants, bleaching agents and/or builders. In the present context "cellulosic material" refers to any material comprising cellulose or derivatives thereof as a significant component. The cellulosic material is contacted with an effective amount of the fusion protein under suitable conditions, such as appropriate pH, and temperature, and the reaction is allowed to continue for a time sufficient for the enzymatic reaction to take place.

The fusion enzymes are especially useful in the treatment of textile materials, such as fabrics and garments. The textile material may be manufactured of natural cellulose containing fibers or man-made cellulose containing fibers or mixtures thereof, or a blend of synthetic fibers and cellulose containing fibers. Preferably, the cellulose containing material is cotton, especially denim. By "denim" is meant, in connection of this invention, denim fabric, usually denim garments, particularly jeans. Advantageously the denim is Indigo dyed denim. Denim can also be treated with derivatives of Indigo or with Indigo together with some other dye, for example Indigo-dyed denim with sulphur bottom.

The fusion endoglucanases are especially useful in biostoning and biofinishing of textiles.

Stone washing has three steps: desizing, abrasion and after-treatment. The first step, the desizing process is normally the first wet treatment of jeans and means removal of starch or other sizing agents usually applied to the warp yarns to prevent damage during the weaving process. Alpha-amylases are used to remove starch-based sizing agents for improved and uniform wet processing. After desizing the jeans are normally rinsed with water or passed directly to the abrasion step.

The second step, abrasion, can be performed with enzymes or pumice stones or both. In all cases mechanical action is needed to remove the dye, and the treatment is usually carried out in washing machines, like drum washers. The term "abraded" means the appearance of denim fabric, when it has been treated by cellulase enzymes or stones, or both. Synonymous expressions are "stone washed look" or "worn look." As a result of uneven dye removal there are contrasts between dyed areas and areas from which dye has been removed.

Abrasion is generally followed by the third step, after-treatment that includes washing and rinsing steps during which detergents, optical brighteners, bleaching agents or softeners may be used. After the enzymatic treatment the reaction must be stopped in order to prevent damage of the treated materials, for example by temperature and/or pH inactivation, the latter comprising a thorough rinsing and/or detergent wash-off. This ensures that the mechanical strength of the fiber is not further compromised by the continued presence of the enzyme.

As used in the present context the expression "biostoning" of fabric or garment means the use of enzymes in place of, or in addition to, pumice stones for the treatment of fabric or garment, especially denim.

As stated above, treatment with cellulase can completely replace treatment with pumice stones (for example, 1 kg commercial enzyme vs. 100 kg stones). However, cellulase treatment can also be combined with pumice stone treatment, when it is desired to produce a heavily abraded finish. A peach skin effect in which a fine protruding hair-like covering is created is also achieved by a wash combining a neutral cellulase with pumice stones. The fusion proteins described are especially useful to efficiently provide an abraded look and to minimize backstaining in biostoning.

Biostoning is typically performed at about pH 3.0 to 8.0, and preferably at pH 5.0 to 7.0. The temperature of the reaction can range from about 30° C. to 80° C. and is preferably between 50 to 60° C. The liquor ratio (the ratio of the volume of liquid per weight of fabric) may range from about 3:1 to 20:1, preferably 5:1 to 10:1. The treatment time can range between 15 min to 90 min and preferably 30 min to 60 min. It should be emphasized that the enzyme dosage greatly depends on the type of the fabrics, machinery, process conditions (pH, temperature, liquor ratio, treatment time, denim load, process scale) and type of enzyme preparation and like. If desired, pumice stones can be used in combination with the endoglucanase fusion proteins. The enzyme dosage required will then be significantly lower. A person skilled in art is capable in defining suitable dosages and conditions.

The endoglucanase fusion proteins of the present invention provide unexpected advantages in that the enzyme performance is high and the backstaining is low resulting in very good contrast. In addition the fusion proteins are easily manufactured, and they may be used in a relatively broad range of temperature and pH.

Further, the endoglucanase fusion proteins are useful in biofinishing of fabrics and garments. "Biofinishing" refers to the use of enzymes in a controlled hydrolysis of cellulosic fibers in order to modify the fabric or yarn surface in a manner that prevents permanently pilling, improves fabric handle like softness and smoothness, clears the surface structure by reducing fuzzing, which results in clarification of colors, improves the drapability of the fabric, improves moisture absorbency and which may improve also the dyeability.

Enzymatic depilling can be carried out at any stage during textile wet processing, preferably after optional desizing and/or bleaching, and similar conditions as in biostoning can be used.

The endoglucanase fusion proteins possessing also beta-glucanase, hemicellulase or xylanase activity are further useful for improving the quality of animal feed, whereby plant material is treated with the enzymes.

Starch, proteins and lipids can be easily degraded by the digestive system of monogastric animals such as poultry and pigs, whereas the major part of non starch polysaccharides (NSP) including mixed-linked beta-glucans of e.g., barley and oats remain intact due to the lack of such enzyme activities within the animal. Furthermore, the digestibility of other components, particularly animal-based fats, is reduced in the presence of NSP.

Beta-glucanases have been commercially used to alleviate problems caused by mixed-linked beta-glucans of barley and oats. Beta-glucanases are known to reduce intestinal viscosity caused by soluble beta-glucans as well as to release nutrients encapsulated by cell-walls rich in beta-glucans. The use of beta-glucanases improves animal performance, which can be seen as improved weight gain and feed conversion ratio. Also, incidences of sticky droppings in poultry are typically reduced.

Steam pelleting is the main feed processing technology throughout the world. Its advantages over production of mash feeds include easier handling, decrease of toxic substances and organisms, and above all improved feed efficiency. The thermotolerance and high performance of the fusion proteins described herein make them suitable for feed applications.

The invention is illustrated by the following non-limiting examples. It should be understood, however, that the embodiments given in the description above and in the examples are for illustrative purposes only, and that various changes and modifications are possible within the scope of the invention.

EXAMPLE 1

Production of *Thermoascus aurantiacus* ALK04242 EG28 Cellulase in *Trichoderma reesei*

Standard molecular biology methods were used in the isolation and enzyme treatments of DNA (plasmids, DNA fragments), in *E. coli* transformations, etc. The basic methods used are described in the standard molecular biology handbooks, e.g., Sambrook et al. (1989) and Sambrook and Russell (2001).

The *Thermoascus aurantiacus* cel5A gene (SEQ ID NO: 1) encoding EG28 cellulase (SEQ ID NO: 2) was amplified by PCR directly from the *T. aurantiacus* ALK04242 genomic DNA, isolated by the method of Raeder and Broda (1985). The forward (SEQ ID NO: 9) and reverse (SEQ ID NO: 10) primers were designed on the basis of the published *T. aurantiacus* endoglucanase sequence (AF487830). The amplified 1.3 kb product containing the exact gene (from START to STOP codon) was cloned as a SacII-PstI fragment into the pBluescript II KS+vector. Two independent clones were sequenced and one clone was selected and designated as pALK1926. The deposit number of the *E. coli* strain containing pALK1926 in the Deutsche Sammlung von Mikroorganismen und Zellkulturen GmbH culture collection is DSM 17326.

An expression plasmid (pALK1930, FIG. 1) was constructed for production of recombinant *T. aurantiacus* cellulase EG28/Cel5A (SEQ ID NO: 2). The cel5A gene, including its own signal sequence, was exactly fused to the *T. reesei* cbh1 (cel7A) promoter by PCR. The cbh1 promoter, cbh1 terminator and amdS marker gene were included as described in Paloheimo et al. (2003). The linear expression cassette (FIG. 1) was isolated from the vector backbone by restriction enzyme digestion, transformed into *T. reesei* A96, and transformants were selected with acetamide as sole nitrogen source. The host strain lacks four major endogenous cellulases: CBHI/Cel7A, CBHII/Cel6A, EGI/Cel7B and EGII/Cel5A. Transformations were performed according to Penttilä et al. (1987) with the modifications described in Karhunen et al. (1993). The transformants were purified on selection plates through single conidia prior to sporulating them on PD.

The cellulase production of the transformants was analyzed from the culture supernatants of shake flask cultivations (50 ml). Transformants were grown for 7 days in a complex cellulose-inducing medium (Joutsjoki et al. 1993) buffered with 5% $KH_2PO_4$ at pH 5.5. The enzyme activity of the recombinant protein was measured from the culture supernatant as the release of reducing sugars from carboxymethylcellulose (2% CMC) at 50° C. in 50 mM Sitrate buffer pH 4.8 essentially as described by Bailey and Nevalainen 1981; Haakana et al. 2004. Activity against barley beta-glucan (1%) was also determined by measuring the release of reducing sugars at 50° C. in 50 mM acetate buffer pH 4.8 as described by Stålbrand et al. 1993. Production of the recombinant protein was also detected from the culture supernatant by SDS-polyacrylamide gel electrophoresis. The genotypes of the chosen transformants were analysed by Southern blotting using the expression cassette as a probe.

Figure 2:
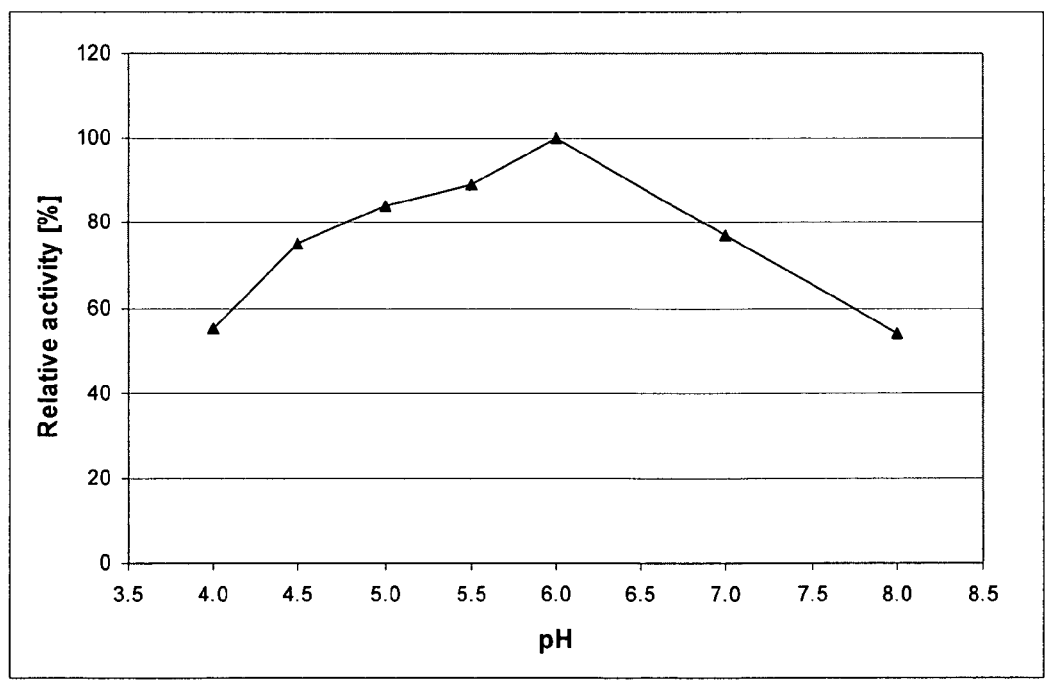
FIG. 2 illustrates the pH dependency of the heterologously produced *T. aurantiacus* EG28 cellulase by determining from the culture supernatant using CMC as substrate in a 10 min reaction at 50° C. (A). Temperature optimum of EG28 cellulase was determined at optimal pH (6.0). The reaction containing CMC as substrate was performed for 10 min (B). The pH and temperature optimum of the EG28+CtCBD fusion protein was determined to be the same as those of the wild-type EG28 cellulase.
Figure 2:
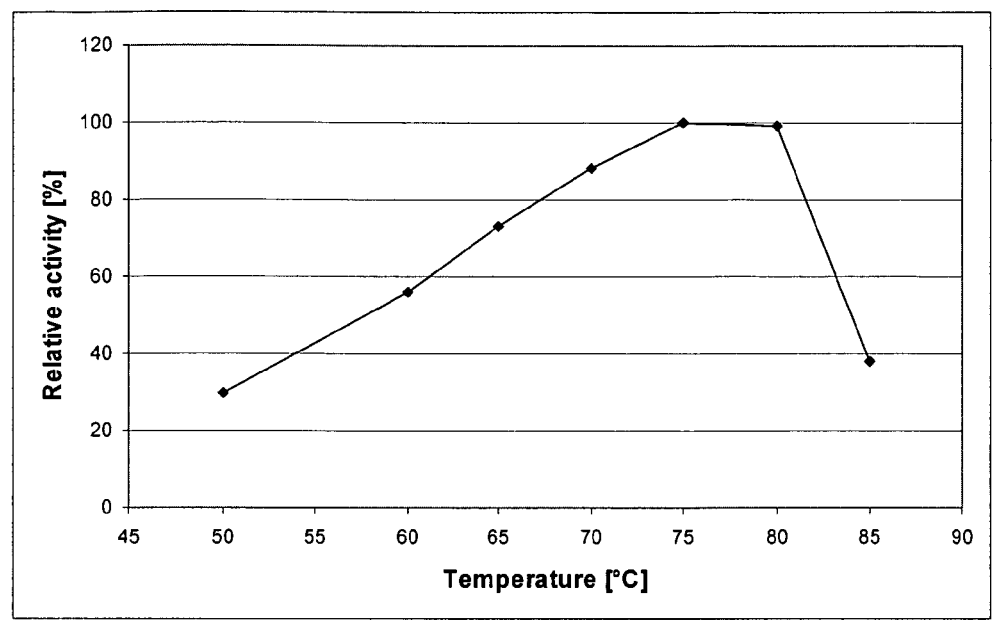

The pH optimum of the heterologously produced Ta EG28/Cel5A cellulase was determined in the universal McIlvaine's buffer within a pH range of 4.0 to 8.0 using carboxymethylcellulose as substrate. As shown in FIG. 2A the pH optimum for EG28/Cel5A cellulase activity is at pH 6.0. The optimal temperature for the enzymatic activity of EG28/Cel5A cellulase was determined to be 75° C. (FIG. 2B).

The chosen transformant (RF6188) was cultivated in a bioreactor to obtain material for the application tests (see Example 4).

EXAMPLE 2

Production of the Recombinant *Thermoascus aurantiacus* ALK04242 EG28+CtCBD Fusion Protein To produce a recombinant *Thermoascus aurantiacus* EG28+CtCBD fusion protein (SEQ ID NO: 4), the cellulose binding domain (CBD) of the CBHI/Cel7A cellulase of *Chaetomium thermophilum* ALKO4265 was linked to the EG28/Cel5A cellulase. The construct contains the catalytic domain of EG28 (amino acids 1-334 of the full-length polypeptide) attached to the linker region and CBD of *C. thermophilum* CBHI/Cel7A CtCBD (SEQ ID NO: 15).

Standard molecular biology methods were used as described in Example 1. First, a unique SnaBI restriction site near the C-terminal end of the EG28/Cel5A sequence was introduced by PCR. This enables direct fusion of any blunt-ended DNA after amino acid Y334 of the EG28/Cel5A polypeptide. The linker and CBD region of the *C. thermophilum* CBHI/Cel7A encoding gene (cel7A, SEQ ID NO: 7) was amplified by PCR using forward (SEQ ID NO: 11) and reverse (SEQ ID NO: 12) primers and *C. thermophilum* ALKO4265 genomic DNA as template. The amplified 1.6 kb product was ligated to the cel5A gene (after Y334) to create Ta cel5A_Ct cel7AlinkerCBD (SEQ ID NO: 3). The resulting plasmid was designated as pALK1946. The deposit number of the *E. coli* strain containing pALK1946 in the Deutsche Sammlung von Mikroorganismen und Zellkulturen GmbH culture collection is DSM 18159.

An expression plasmid (pALK1948, FIG. 1) for production of the EG28+CtCBD cellulase was constructed as described in Example 1. The linear 8.9 kb expression cassette (FIG. 1) was isolated from the vector backbone by NotI restriction enzyme digestion, transformed into *T. reesei* A33 (the strain has the genes encoding the four major cellulases CBHI/Cel7A, CBHII/Cel6A, EGI/Cel7B and EGII/Cel5A deleted), and transformants selected as described in Example 1. The pH and temperature optimum of the fusion protein was determined to be the same as those of the wild-type EG28 protein.

The chosen transformant (RF6377) was cultivated in a bioreactor to obtain material for the application tests (see Examples 5 to 10).

EXAMPLE 3

Production of the Recombinant *Acremonium thermophilum* ALK04245 EG40+CtCBD Fusion Protein For production of a recombinant *Acremonium thermophilum* ALK04245 EG40+CtCBD fusion protein (SEQ ID NO: 6), the cellulose binding domain of EG40 cellulase is replaced with that of the *Chaetomium thermophilum* ALKO4265 CBHI/Cel7A. The construct contains the catalytic domain of EG40 cellulase (amino acids 1 to 234 of the full-length polypeptide) attached to the linker region and CBD of *C. thermophilum* CBHI/Cel7A (CtCBD, SEQ ID NO: 15).

Standard molecular biology methods are used as described in Example 1. The *Acremonium thermophilum* cel45A gene (SEQ ID NO: 8) is amplified by PCR from the *A. thermophilum* ALKO4245 genomic DNA using primers (SEQ ID NO: 13) and (SEQ ID NO: 14). The 1.1 kb PCR fragment is cloned as a SacII-PstI fragment into the pBluescript II KS+ vector. After this, a unique NruI restriction site near the C-terminal end of the EG40 sequence is introduced by PCR. This enables direct fusion of any blunt-ended DNA after amino acid S234 of the EG40 polypeptide. The linker plus CBD region of the CBHI/Cel7A cellulase of *Chaetomium thermophilum* (cel7A) is amplified by PCR as described in Example 2 and a restriction fragment thereof ligated to the cel45A gene (after S234) to create At cel45A_Ct cel7AlinkerCBD (SEQ ID NO: 5). An expression plasmid for production of the EG40+CtCBD cellulase is constructed and the recombinant protein (SEQ ID NO: 6) is produced in *Trichoderma* as described in Example 1.

EXAMPLE 4

Performance of EG28 Cellulase in Denim Finishing at Different Temperatures

*Thermoascus aurantiacus* EG28 cellulase produced in *Trichoderma* (strain RF6188) as described in Example 1 was tested for its ability to create an abraded look similar to that provided by pumice stones in biostoning of denim at different temperatures. An efficient denim finishing enzyme, a commercial EGII enriched acid cellulase preparation produced in *Trichoderma* (U.S. Pat. No. 5,874,293) was used as a reference.

Jeans made of Indigo dyed denim twill were used as test material after desizing with ECOSTONE® A200 alpha-amylase. The cellulase treatments were performed with Electrolux's Wascator FOM 71 CLS washer extractor under conditions described in Table 1.

The endoglucanase activity (ECU) of the enzyme preparations used was measured as the release of reducing sugars from hydroxyethyl cellulose as previously described (Bailey and Nevalainen, 1981). The EGII enriched enzyme concentrate and EG28 preparation were dosed at 220 ECU/g and ca. 380 ECU/g fabric, respectively. The enzymes were tested at their optimal pH range, the EGII preparation at pH 5 and the EG28 preparation at pH 6. After draining, the enzyme was inactivated (for 10 minutes at 40° C.) by raising the pH above 11 with sodium hydroxide. The jeans were then rinsed three times with water and dried in a tumbler.

The biostoning effect/abrasion level was evaluated by measuring the color as reflectance values with a Minolta CM 2500 spectrophotometer using L*a*b* color space coordinates (illuminant D65/2°). The color from the face and the reverse side of denim and of the pockets was measured after desizing (i.e. before cellulase treatment) and after the cellulase treatment. Each measurement on the face side, reverse side or pockets was the average of approximate 40, 20, or 12 measurements, respectively. Two pairs of jeans were used in each test and the final result was the average thereof. The results are shown in Table 2 and FIG. 3.

TABLE 1

Test conditions/process parameters used in cellulase treatments.

| Process parameter | |
|---|---|
| Denim load | 1.3 kg |
| Water | 19 liter |
| pH control (pH 5-5.3) | 35 g $Na_2HPO_4 2H_2O$ + 22 g citric acid |
| pH control (pH 6.1-6.3) | 35.5 g $Na_2HPO_4 2H_2O$ + 15 g citric acid |

TABLE 1-continued

Test conditions/process parameters used in cellulase treatments.

| Process parameter | |
|---|---|
| Time | 45 min |
| Temperature | 40, 50, 60 or 70° C. |
| Cellulase dosage | 220 or ca. 380 ECU/g fabric |

TABLE 2

Color measurements of denim treated with EG28 cellulase at different temperatures.

| Enzyme preparation | ECU/g garment | Conditions | Before cellulase Treatment L* | Before cellulase Treatment b* | After cellulase Treatment L* | After cellulase Treatment b* | deltaL* | deltab* |
|---|---|---|---|---|---|---|---|---|
| Face side: | | | | | | | | |
| EG28 | 380 | 70° C., pH 6.1-6.3 | 23.67 | −16.07 | 32.63 | −16.94 | 8.96 | −0.87 |
| EG28 | 370 | 60° C., pH 6.1-6.3 | 23.67 | −16.38 | 31.94 | −17.09 | 8.27 | −0.71 |
| EG28 | 380 | 50° C., pH 6.1-6.3 | 23.62 | −16.24 | 31.91 | −16.86 | 8.30 | −0.63 |
| EG28 | 380 | 40° C., pH 6.1-6.3 | 23.75 | −16.07 | 30.57 | −17.32 | 6.82 | −1.25 |
| EGII enriched | 220 | 60° C., pH 5.2-5.3 | 23.45 | −16.10 | 32.90 | −17.29 | 9.46 | −1.19 |
| Reverse side: | | | | | | | | |
| EG28 | 380 | 70° C., pH 6.1-6.3 | 49.76 | −6.95 | 49.60 | −10.43 | −0.16 | −3.48 |
| EG28 | 370 | 60° C., pH 6.1-6.3 | 49.55 | −6.87 | 50.78 | −9.57 | 1.24 | −2.71 |
| EG28 | 380 | 50° C., pH 6.1-6.3 | 49.92 | −7.05 | 50.49 | −9.83 | 0.57 | −2.78 |
| EG28 | 380 | 40° C., pH 6.1-6.3 | 49.89 | −6.93 | 49.73 | −9.73 | −0.16 | −2.80 |
| EGII enriched | 220 | 60° C., pH 5.2-5.3 | 49.75 | −6.82 | 48.28 | −12.26 | −1.47 | −5.45 |
| Pockets: | | | | | | | | |
| EG28 | 380 | 70° C., pH 6.1-6.3 | 77.40 | −8.14 | 68.53 | −12.60 | −8.86 | −4.47 |
| EG28 | 374 | 60° C., pH 6.1-6.3 | 77.91 | −7.71 | 70.29 | −12.34 | −7.62 | −4.63 |
| EG28 | 380 | 50° C., pH 6.1-6.3 | 78.11 | −7.62 | 70.63 | −12.02 | −7.49 | −4.40 |
| EG28 | 380 | 40° C., pH 6.1-6.3 | 77.51 | −7.60 | 70.47 | −11.91 | −7.04 | −4.32 |
| EGII enriched | 220 | 60° C., pH 5.2-5.3 | 77.46 | −7.68 | 66.18 | −14.17 | −11.29 | −6.49 |

Treatment with EGII enriched preparation was used as reference.
L* indicates the lightness, −b* is the blue direction, +b* is the yellow direction.

Figure 3:
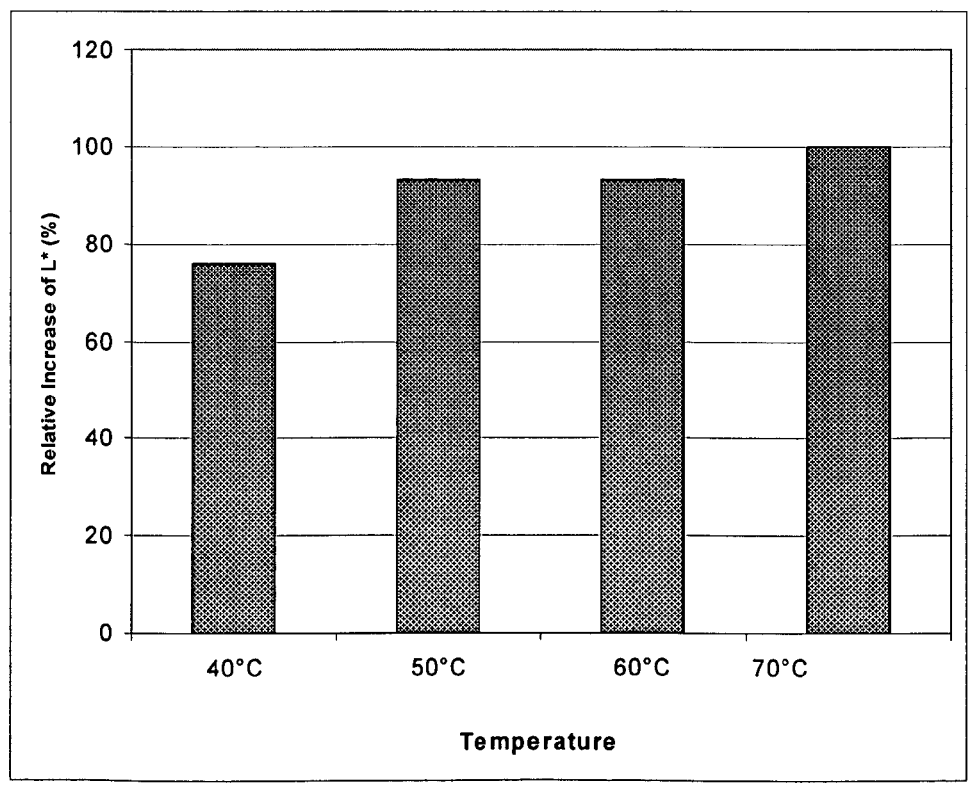
FIG. 3 shows the biostoning effect of EG28 cellulase, by measuring the color, at different temperatures and pH 6.

The results in Table 2 and FIG. 3 show that the best abrasion effect with the EG28 preparation (strain RF6188) was obtained at the range of 50 to 70° C. Using a dosage of 380 ECU/g fabric of the EG28 preparation at 70° C. a similar abrasion level (lightness L*) was obtained compared to using the dosage of 220 ECU/g fabric of an EGII enriched preparation at 60° C. However, the back-staining effect (re-deposition of Indigo-dye) on the reverse side of the denim and pockets was lower with the EG28 preparation (higher lightness, less blue) than with the EGII enriched preparation. Also the contrast on the face side of the denim looked better.

EXAMPLE 5

Performance of EG28+CtCBD Fusion Protein Compared to EG28 Cellulase in Denim Finishing Recombinant *Thermoascus aurantiacus* EG28+CtCBD fusion protein produced in *Trichoderma* (strain RF6377) as described in Example 2 was compared to the EG28 preparation from strain RF6188 in biostoning of denim at pH 6, 60° C. The denim and test system for biostoning were as in Example 4, except that the amount of denim was leveled to 1430 g with an extra piece of different denim that was not included in the measurements. The effect of the cellulase treatment was evaluated as in Example 4.

The results in Table 3 show that the biostoning effect of the EG28+CtCBD preparation was very good at a low dosage. With strain RF6377 a similar abrasion level (lightness L*) was obtained with 6.5 times lower dosage compared to RF6188. Linking of cellulose binding domain (CBD) to EG28 cellulase did not increase the undesirable backstaining effect, but increased the desired washing performance greatly.

TABLE 3

Color measurements of denim treated with EG28 and EG28 + CtCBD cellulases at 60° C., pH 6.

| Enzyme preparation | ECU/g garment | Before cellulase treatment L* | Before cellulase treatment b* | After cellulase Treatment L* | After cellulase Treatment b* | deltaL* | deltab* |
|---|---|---|---|---|---|---|---|
| Face side: | | | | | | | |
| EG28 | 325 | 23.40 | −16.02 | 31.01 | −17.12 | 7.62 | −1.10 |
| EG28 + CtCBD | 50 | 23.81 | −16.21 | 31.60 | −16.92 | 7.80 | −0.71 |

TABLE 3-continued

Color measurements of denim treated with EG28 and EG28 + CtCBD cellulases at 60° C., pH 6.

| Enzyme preparation | ECU/g garment | Before cellulase treatment | | After cellulase Treatment | | | |
|---|---|---|---|---|---|---|---|
| | | L* | b* | L* | b* | deltaL* | deltab* |
| Reverse side: | | | | | | | |
| EG28 | 325 | 49.46 | −6.83 | 50.03 | −9.62 | 0.57 | −2.79 |
| EG28 + CtCBD | 50 | 49.36 | −7.03 | 50.62 | −9.61 | 1.27 | −2.58 |
| Pockets: | | | | | | | |
| EG28 | 325 | 76.11 | −8.36 | 68.53 | −12.46 | −7.58 | −4.10 |
| EG28 + CtCBD | 50 | 76.02 | −8.45 | 68.81 | −12.39 | −7.21 | −3.94 |

L* indicates the lightness, −b* is the blue direction, +b* is the yellow direction.

EXAMPLE 6

Performance of EG28+CtCBD Cellulase Compared to EGII Cellulase in Denim Finishing Recombinant *Thermoascus aurantiacus* EG28+CtCBD fusion protein produced in *Trichoderma* (strain RF6377) was compared to the commercial EGII enriched acid cellulase preparation (U.S. Pat. No. 5,874,293) in biostoning of denim.

The test system for biostoning was as in Example 4, except that pieces (legs) of several different Denim types from Ukos Sport (Belgium) and Vicunha (Brazil) were used (total 1.2 kg). The conditions for EG28+CtCBD and EGII treatment were as in Table 4. The effect of the cellulase treatment was evaluated as in Example 4.

The results of the experiments performed with four different denim fabrics are shown in Tables 4 and 5. Using an enzyme dosage of 500 ECU/g fabric of EG28+CtCBD preparation a similar lightness level was obtained compared to using a dosage of 1000 ECU/g of the EGII enriched preparation. The performance of the EG28+CtCBD preparation required roughly only half of the ECU-activity of that of EGII enriched cellulase. Also the culture medium of EG28+CtCBD produced by the recombinant host is volumetrically about two-fold as effective as that of the EGII producing recombinant host in biostoning. Considerably less backstaining was observed on the reverse side of the denim when EG28+CtCBD preparation was used. The performance of the EG28+CtCBD preparation at 50° C. was better at pH 6 than at pH 5.

TABLE 4

Color measurements on the face side off denim treated with EG28 + CtCBD cellulase at pH 5 and 6.

| Enzyme preparation | Denim | ECU/g garment | Conditions | Before cellulase Treatment | | After cellulase treatment | | | |
|---|---|---|---|---|---|---|---|---|---|
| | | | | L* | b* | L* | b* | deltaL* | deltab* |
| EGII Enriched | Atlanta, Ukos sport | 1000 | pH adj. with acetic acid 55 min, 50° C., pH 5 | 19.96 | −15.91 | 27.44 | −18.49 | 7.48 | −2.58 |
| | Mathew, Ukos sport | | | 18.28 | −7.97 | 21.87 | −11.71 | 3.59 | −3.74 |
| | Nostalgy, Ukos sport | | | 19.12 | −8.78 | 23.90 | −13.50 | 4.78 | −4.72 |
| | Vicunha, Savana | | | 17.24 | −10.49 | 21.51 | −14.93 | 4.27 | −4.44 |
| | Average | | | 18.65 | −10.79 | 23.68 | −14.66 | 5.03 | −3.87 |
| EG28 + CtCBD | Atlanta, Ukos sport | 500 | pH adj. with acetic acid 55 min, 50° C., pH 5 | 19.79 | −16.02 | 25.88 | −18.44 | 6.09 | −2.42 |
| | Mathew, Ukos sport | | | 18.07 | −8.58 | 21.45 | −11.80 | 3.38 | −3.22 |
| | Nostalgy, Ukos sport | | | 19.05 | −8.73 | 22.65 | −12.69 | 3.60 | −3.96 |
| | Vicunha, Savana | | | 17.38 | −10.11 | 20.75 | −14.18 | 3.37 | −4.07 |
| | Average | | | 18.57 | −10.86 | 22.68 | −14.28 | 4.11 | −3.42 |
| EG28 + CtCBD | Atlanta, Ukos sport | 500 | pH adj. with acetic acid 55 min, 50° C., pH 6 | 19.98 | −16.18 | 27.35 | −18.20 | 7.37 | −2.02 |
| | Mathew, Ukos sport | | | 17.51 | −8.84 | 21.40 | −11.62 | 3.89 | −2.78 |
| | Nostalgy, Ukos sport | | | 18.58 | −8.65 | 22.96 | −12.75 | 4.38 | −4.10 |
| | Vicunha, Savana | | | 17.50 | −10.16 | 21.49 | −14.06 | 3.99 | −3.90 |
| | Average | | | 18.39 | −10.96 | 23.30 | −14.16 | 4.91 | −3.20 |

Treatment with EGII enriched preparation was used for comparison.
L* indicates the lightness, −b* is the blue direction, +b* is the yellow direction.

TABLE 5

Color measurements on the reverse side of denim treated with EG28 + CtCBD cellulase at pH 5 and 6.

| Enzyme preparation | Denim | ECU/g garment | Conditions | Before cellulase treatment L* | b* | After cellulase treatment L* | b* | deltaL* | deltab* |
|---|---|---|---|---|---|---|---|---|---|
| EGII Enriched | Atlanta, Ukos sport | 1000 | pH adj. with acetic acid 55 min, 50° C., pH 5 | 47.98 | −7.25 | 40.18 | −14.63 | −7.80 | −7.38 |
| | Mathew, Ukos sport | | | 38.41 | −7.17 | 36.11 | −10.93 | −2.30 | −3.76 |
| | Nostalgy, Ukos sport | | | 46.70 | −6.06 | 41.87 | −11.73 | −4.83 | −5.67 |
| | Vicunha, Savana | | | 35.65 | −9.24 | 33.48 | −12.44 | −2.17 | −3.20 |
| | Average | | | 42.19 | −7.43 | 37.91 | −12.43 | −4.28 | −5.00 |
| EG28 + CtCBD | Atlanta, Ukos sport | 500 | pH adj. with acetic acid 55 min, 50° C., pH 5 | 48.01 | −7.29 | 41.82 | −13.25 | −6.19 | −5.96 |
| | Mathew, Ukos sport | | | 37.60 | −7.27 | 35.59 | −10.50 | −2.01 | −3.23 |
| | Nostalgy, Ukos sport | | | 46.79 | −5.99 | 44.75 | −9.37 | −2.04 | −3.38 |
| | Vicunha, Savana | | | 35.08 | −9.48 | 33.72 | −11.80 | −1.36 | −2.32 |
| | Average | | | 41.87 | −7.51 | 38.97 | −11.23 | −2.90 | −3.72 |
| EG28 + CtCBD | Atlanta, Ukos sport | 500 | pH adj. with acetic acid 55 min, 50° C., pH 6 | 47.55 | −7.43 | 42.41 | −13.30 | −5.14 | −5.87 |
| | Mathew, Ukos sport | | | 37.27 | −7.58 | 36.01 | −10.27 | −1.26 | −2.69 |
| | Nostalgy, Ukos sport | | | 47.02 | −6.01 | 44.61 | −10.13 | −2.41 | −4.12 |
| | Vicunha, Savana | | | 34.84 | −9.39 | 33.53 | −11.20 | −1.31 | −1.81 |
| | Average | | | 41.67 | −7.60 | 39.14 | −11.23 | −2.53 | −3.62 |

Treatment with EGII enriched preparation was used for comparison.
L* indicates the lightness, −b* is the blue direction

EXAMPLE 7

Effect of pH on the Performance of EG28+CtCBD Cellulase Preparation at 50° C. and 60° C.

Recombinant *Thermoascus aurantiacus* EG28+CBD fusion protein produced in *Trichoderma* (strain RF6377) was tested for its performance in biostoning of denim at different pH values at 50° C. and 60° C.

Indigo dyed denim twill (different from the previous examples) that was desized and cut into pieces was used as test material. Cellulase treatments were performed in LP-2 Launder Ometer as follows. About 7.2 g of denim fabric (ca. 12 cm×12 cm swath), 200 ml of Mc Ilvaine's citrate phosphate buffer, and 90 steel balls (diameter 0.6 cm) were loaded into 1.2 liter containers. The Launder Ometer was run for 120 min at different pH values of 4 to 8 using temperatures 50° C. and 60° C. After removing the swathes from the containers they were rinsed with water and soaked in water containing NaOH (pH>11) for 10 min with mixing. Thereafter, the swathes were soaked in warm water containing liquid detergent (OMO Color) and mixed for 10 min, followed by careful rinsing with warm water for several times. The swathes were dried at room temperature. The biostoning effect was evaluated by measuring the color as reflectance units as described in Example 4. Each measurement value on the face side of denim swath was the average of at least 20 measurements.

Figure 4:
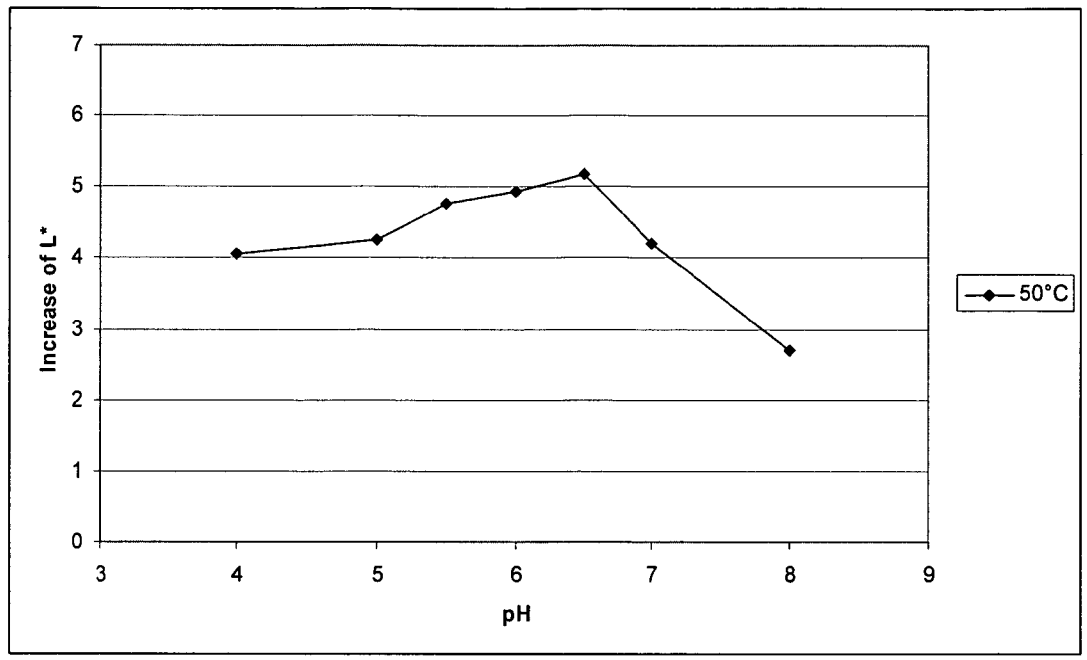
FIG. 4 shows the biostoning effect of EG28+CtCBD cellulase, by measuring the color, at different pH-values at 50° C.
Figure 5:
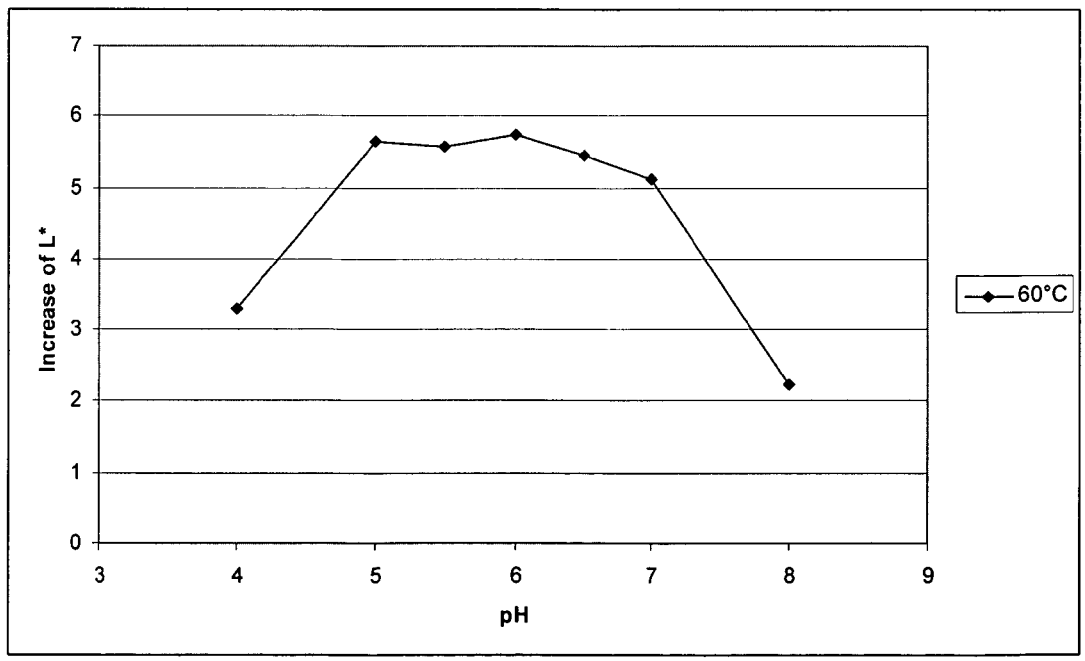
FIG. 5 shows the biostoning effect of EG28+CtCBD cellulase, by measuring the color, at different pH-values at 60° C.

The results shown in Tables 6 and 7 and FIGS. 4 and 5 show that the most optimal pH range for the EG28+CtCBD cellulase at 50° is 5.5 to 6.5 and at 60° C. 5 to 7.

TABLE 6

Color measurements on the face side of denim treated with EG28 + CtCBD cellulase at different pH values in Launder at 50° C.

| Enzyme preparation | ECU/g garment | Conditions | Before cellulase Treatment L* | b* | After cellulase treatment L* | b* | Increase of L* |
|---|---|---|---|---|---|---|---|
| Buffer Control | 0 | pH 6 | 17.28 | −13.07 | 18.77 | −14.13 | 1.49 |
| Buffer Control | 0 | pH 8 | 17.01 | −13.4 | 18.18 | −14.45 | 1.17 |
| EG28 + CtCBD | 1000 | pH 4 | 16.79 | −13.59 | 20.86 | −16.40 | 4.07 |
| EG28 + CtCBD | 1000 | pH 5 | 17.34 | −13.18 | 21.59 | −16.44 | 4.25 |
| EG28 + CtCBD | 1000 | pH 5.5 | 17.30 | −13.25 | 22.06 | −16.39 | 4.76 |
| EG28 + CtCBD | 1000 | pH 6 | 17.35 | −13.42 | 22.29 | −16.47 | 4.94 |
| EG28 + CtCBD | 1000 | pH 6.5 | 17.31 | −13.41 | 22.48 | −16.65 | 5.17 |
| EG28 + CtCBD | 1000 | pH 7 | 17.34 | −13.25 | 21.55 | −16.23 | 4.21 |
| EG28 + CtCBD | 1000 | pH 8 | 16.91 | −13.63 | 19.62 | −15.72 | 2.71 |

L* indicates the lightness, −b* is the blue direction

TABLE 7

Color measurements on the face side of denim treated with EG28 + CtCBD cellulase at different pH values in Launder at 60° C.

| Enzyme preparation | ECU/g garment | Conditions | Before cellulose L* | b* | After cellulase L* | b* | Increase of L* |
|---|---|---|---|---|---|---|---|
| EG28 + CtCBD | 1000 | pH 4 | 17.19 | −13.58 | 20.48 | −15.77 | 3.29 |
| EG28 + CtCBD | 1000 | pH 5 | 17.10 | −13.24 | 22.74 | −16.59 | 5.64 |
| EG28 + CtCBD | 1000 | pH 5.5 | 17.10 | −13.54 | 22.66 | −16.61 | 5.56 |
| EG28 + CtCBD | 1000 | pH 6 | 17.10 | −13.65 | 22.83 | −16.74 | 5.73 |
| EG28 + CtCBD | 1000 | pH 6.5 | 17.19 | −13.47 | 22.65 | −11.72 | 5.46 |
| EG28 + CtCBD | 1000 | pH 7 | 16.99 | −13.72 | 22.10 | −16.66 | 5.11 |
| EG28 + CtCBD | 1000 | pH 8 | 17.13 | −13.68 | 19.35 | −15.15 | 2.22 |
| Buffer Control | 0 | pH 6 | 17.36 | −13.6 | 18.95 | −14.28 | 1.59 |

L* indicates the lightness, −b* is the blue direction

EXAMPLE 8

Performance of EG28+CtCBD Cellulase Preparation in Denim Finishing at Different Temperatures Recombinant *Thermoascus aurantiacus* EG28+CtCBD fusion protein produced in *Trichoderma* (strain RF6377) as described in Example 1 was tested for its ability to create an abraded look similar to that provided by pumice stones in biostoning of denim at different temperatures. Efficient denim finishing enzymes, commercial EGII enriched acid cellulase preparation (U.S. Pat. No. 5,874,293) and neutral cellulase preparation ECOSTONE® C1 were used as reference.

The test system for biostoning was as in Example 4, except that different Denim twill and a washing time of 55 min were used. The enzymatic activity (endoglucanase unit, ECU) of the EG28+CtCBD and EGII enriched enzyme preparations was measured as in Example 4. The activity (neutral cellulase unit, NCU) of the neutral cellulase preparation ECOSTONE® C1 was measured as the release of reducing sugars from carboxymethyl cellulose as previously described (Bailey and Nevalainen, 1981; Haakana et al. 2004). The ECOSTONE® C1, EG28+CtCBD, or EGII enriched preparations were dosed at 250 NCU/g, 500 ECU/g, or 1000 ECU/g fabric, respectively. The effect of the cellulase treatment was evaluated as in Example 4.

Figure 6:
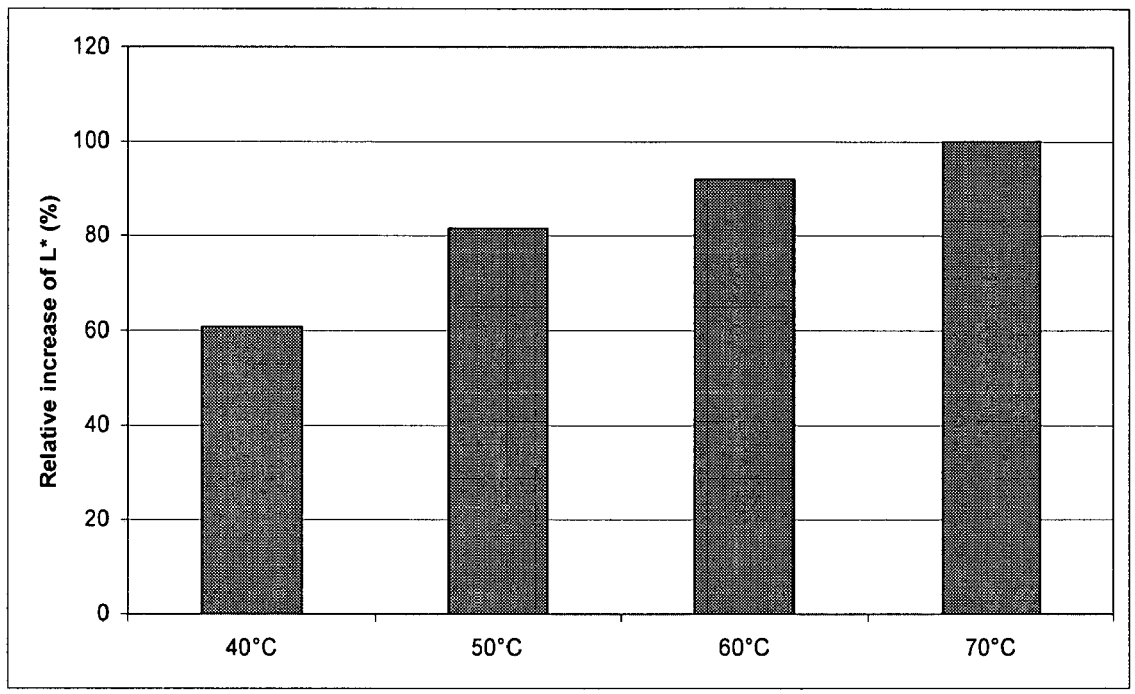
FIG. 6 shows the biostoning effect of EG28+CtCBD cellulase, by measuring the color, at different temperatures (pH 6).

The performance of EG28+CtCBD at temperatures of 40 to 70° C., pH 6 is shown in Table 8 and FIG. 6. The preferred temperature range for the enzyme is 50 to 70° C. Lower temperatures like 40° C. can be used to obtain an abrasion effect with less color pull if a darker look is desirable.

The results are also in agreement with those obtained in Example 6, where the performance of EG28+CtCBD in biostoning was shown to be about two times more effective than that of the commercial EGII enriched acid cellulase preparation. Acid cellulases generally have a tendency of backstaining. Neutral cellulases, like ECOSTONE® C1, typically cause low backstaining therefore resulting in good contrast. The results obtained here show that a similar effect was obtained with the EG28+CtCBD cellulase as with the neutral cellulases (Table 8).

TABLE 8

Color measurements of denim treated with EG28 + CtCBD cellulase at different temperatures.

| Enzyme preparation | Activity/g garment | Conditions | Before cellulase Treatment L* | b* | After cellulase Treatment L* | b* | deltaL* | deltab* |
|---|---|---|---|---|---|---|---|---|
| Face side: | | | | | | | | |
| EG28 + CBD | 500 ECU/g | 70 C. °, pH 6.2 | 17.38 | −13.49 | 27.42 | −17.27 | 10.05 | −3.78 |
| EG28 + CBD | 500 ECU/g | 60 C. °, pH 6.2 | 16.76 | −13.31 | 26.01 | −17.49 | 9.25 | −4.18 |
| EG28 + CBD | 500 ECU/g | 50 C. °, pH 6.2 | 16.78 | −13.40 | 25.00 | −17.44 | 8.22 | −4.04 |
| EG28 + CBD | 500 ECU/g | 40 C. °, pH 6.2 | 16.76 | −13.21 | 22.86 | −17.25 | 6.11 | −4.04 |
| EGII enriched | 1000 ECU/g | 60 C. °, pH 5.1 | 17.24 | −13.38 | 26.59 | −17.64 | 9.35 | −4.26 |
| ECOSTONE C1 | 250 NCU/g | 60 C. °, pH 6.5 | 17.38 | −13.53 | 26.91 | −16.98 | 9.53 | −3.45 |
| Reverse side: | | | | | | | | |
| EG28 + CBD | 500 ECU/g | 70 C. °, pH 6.2 | 45.67 | −6.33 | 41.78 | −13.83 | −3.90 | −7.51 |
| EG28 + CBD | 500 ECU/g | 60 C. °, pH 6.2 | 45.60 | −5.95 | 42.72 | −13.05 | −2.88 | −7.10 |
| EG28 + CBD | 500 ECU/g | 50 C. °, pH 6.2 | 45.67 | −5.92 | 41.81 | −13.35 | −3.86 | −7.44 |
| EG28 + CBD | 500 ECU/g | 40 C. °, pH 6.2 | 45.80 | −5.72 | 41.66 | −12.52 | −4.14 | −6.81 |
| EGII enriched | 1000 ECU/g | 60 C. °, pH 5.1 | 46.10 | −6.19 | 39.89 | −15.24 | −6.21 | −9.06 |
| ECOSTONE C1 | 250 NCU/g | 60 C. °, pH 6.5 | 45.63 | −6.46 | 42.49 | −12.76 | −3.14 | −6.31 |

Treatment with EGII enriched acid cellulase and ECOSTONE ® C1 neutral cellulase preparation was used as reference.
L* indicates the lightness, −b* is the blue direction, +b* is the yellow direction.

EXAMPLE 9

Performance of EG28 and EG28+CtCBD Cellulases in Biofinishing (Depilling)

The performance of EG28 cellulase from strain RF6188 and EG28+CtCBD preparation from strain RF6377 in depilling of cotton knitwear was tested. The cellulase treatments were performed with Electrolux's Wascator FOM 71 CLS washer extractor under conditions described in Table 9.

Pieces of two kinds of low quality Polo-neck sweaters with fuzzy surface, made of 100% cotton jersey-based fabric or rib made of 95% cotton and 5% of lycra were used as test material with filling material. Samples were first prewashed for 10 min at 60° C. with 1 ml/l surfactants/wetting agents (Sandoclean PCJ from Sandos and Imacol CN from Clariant) and rinsed three times with water. After that the cotton knits were treated with cellulase at 60° C. for 60 minutes, in the presence of the same textile auxiliaries as used in prewash. The enzyme was inactivated as described in Example 4, except for the temperature, which was 60° C. during the alkaline rinse. The pieces of knitwear were rinsed three times and thereafter dried in the tumbler.

TABLE 9

Test conditions/process parameters used in biofinishing treatments.

| Process parameter | |
|---|---|
| Fabric load | 1.0 kg |
| Water | 15 liter |
| Sandoclean PCJ and Imacol CN | 1 ml/l |
| Buffer/pH control (pH 5-5.3) | ca. 3 ml Acetic acid (80%) |
| Time | 60 min |
| Temperature | 60° C. |
| Cellulase dosage | 1200 ECU/g fabric |

The effect of the cellulase treatment was evaluated visually with the naked eye and with a loupe. A prewashed sample without enzyme was used as control.

The results showed that the EG28+CtCBD preparation improved depilling properties. The surface fuzzing of the knitwear was considerably reduced after treatment with the EG28+CtCBD preparation compared to the control (treatment without enzyme). Also the EG28 preparation had a depilling effect.

EXAMPLE 10

Feed Pelleting Stability Test

Two cellulose preparations, EG28 (strain RF6188) and EG28+CtCBD (strain RF6377) were separately tested in an experiment, which simulates an industrial feed production process. Prior to testing the spray-dried EG28 or EG28+CtCBD preparations were ground with wheat flour in order to improve homogeneity at feed level. EG28 or EG28+CtCBD enzymes premixed with flour were added at a dosage of 200 g/t and at 500 g/t of feed, respectively. Enzyme overdosing was used to facilitate analysis from samples pelleted at high temperatures, where activity may have been substantially reduced.

The mill and mixer are used for producing meal mixtures as part of a semi-industrial feed plant with a nominal pelleting capacity of 5 t/h. The mill is a Champion hammer mill equipped with Ø 3.0 mm die. The ground raw material is mixed in a 2,500 litre horizontal mixer at 27 rpm before being transferred to the mini feed milling plant. The plant comprises a horizontal mixer (volume 700 L, speed 48 rpm, mixing batches of 300 kg), a Skjold TR dozing screw and a Kahl cascade mixer (length 130 cm, diameter 30 cm, speed 155 rpm, equipped with 37 adjustable pallets). The dwell time for 300 kg/h is approx. 30 sec. Mounted on the side of the cascade mixer is a manifold with a water discharger and 3 steam valves from which steam is lead to the meal. Steam is provided by a high-pressure boiler with a maximum capacity of 400 kg steam/h. Tests are conducted with 2 atmospheres overpressure and the steam is led via a pressure reduction valve, which controls the addition of steam to the cascade mixer. Three valves on the manifold are used for fine adjustment of the desired meal temperature. Meal temperature is measured by a digital thermometer placed in the outlet of the cascade mixer, just before the meal entered to pellet die. The pellet press is a Simon Heesen, type labor (monoroll) with a Ø 3 mm*35 mm die and a 7.5 kW motor. Internal diameter of die: 173 mm, height of press roll: 50 mm, diameter of press roll: 140 mm, run rate 500 rpm and nominal capacity: 300 kg/h. Samples are taken after the pellet press and cooled in a partitioned cooling box with perforated bottom, ventilator: 1500 $m^3$ air/h.

A 300 kg batch of a wheat-based mash feed was produced. A premix was produced from 10 kg of this meal and 200 g (or 500 g) of the test enzyme in a 70 litre compulsory mixer. Mixer speed: 45 rpm. Mixing time: 10 min. This premix was added with 290 kg of the feed into the horizontal mixer in the mini feed milling plant and mixed for 10 minutes. After sampling of the mash, the feed was pelleted through the pellet press (die Ø 3 mm). The meal was heated to the target temperature (65 to 90° C.) by adjusting steam addition to the cascade mixer. For each temperature, a sample was first taken 10 minutes after the target pelleting temperature (as measured in the meal just prior to pelleting) was achieved. Samples were taken during 1.0 min. corresponding to 5.0 kg of pelleted feed. The sample was taken as sub-samples of approx. 500 grams and placed in a cooling box for 10-15 seconds after the pellets had left the pellet press. All samples were aerated and cooled at ambient temperature for 15 minutes. The samples were homogeneously sub-sampled on a riffler sample divider and filled into plastic bags.

The samples were analysed as follows: 2.5 g of well ground sample and 20 ml of acetate buffer (0.05 M, pH 5.0) buffer were stirred for 30 min at room temperature, centrifuged (10 min, 4000 rpm) and diluted. 1.0 ml of cleared sample in triplicate was equilibrated for 5 min in a water bath at 40° C. The reaction was initiated by addition of a Beta-Glucazyme tablet (Megazyme, Ireland) without stirring. After exactly 30 min the reaction was stopped by adding 5.0 ml of Trizma Base 1% (w/v) (Sigma-Aldrich) with vigorous stirring on a vortex mixer. The tube was left at room temperature for about 5 min; the slurry was stirred again and filtered through Whatman 1 filter paper. The absorbance of the filtrate was measured at 590 nm. The results were analyzed using a standard curve.

Figure 7:
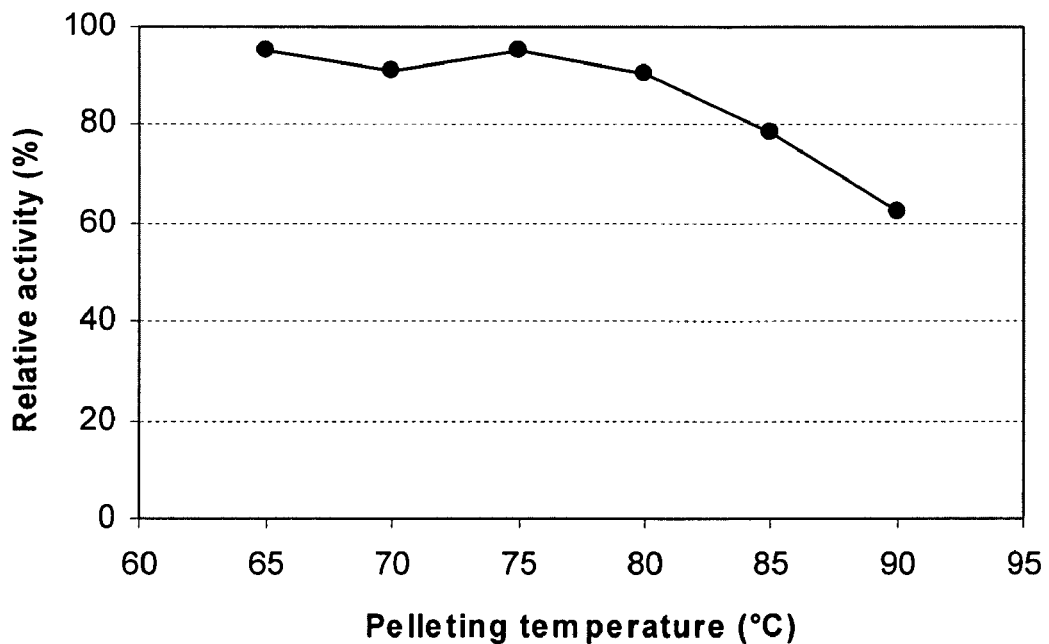
FIG. 7 shows the Influence of the pelleting temperature on beta-glucanase activity recovery of feeds supplemented with EG28 cellulase.
Figure 8:
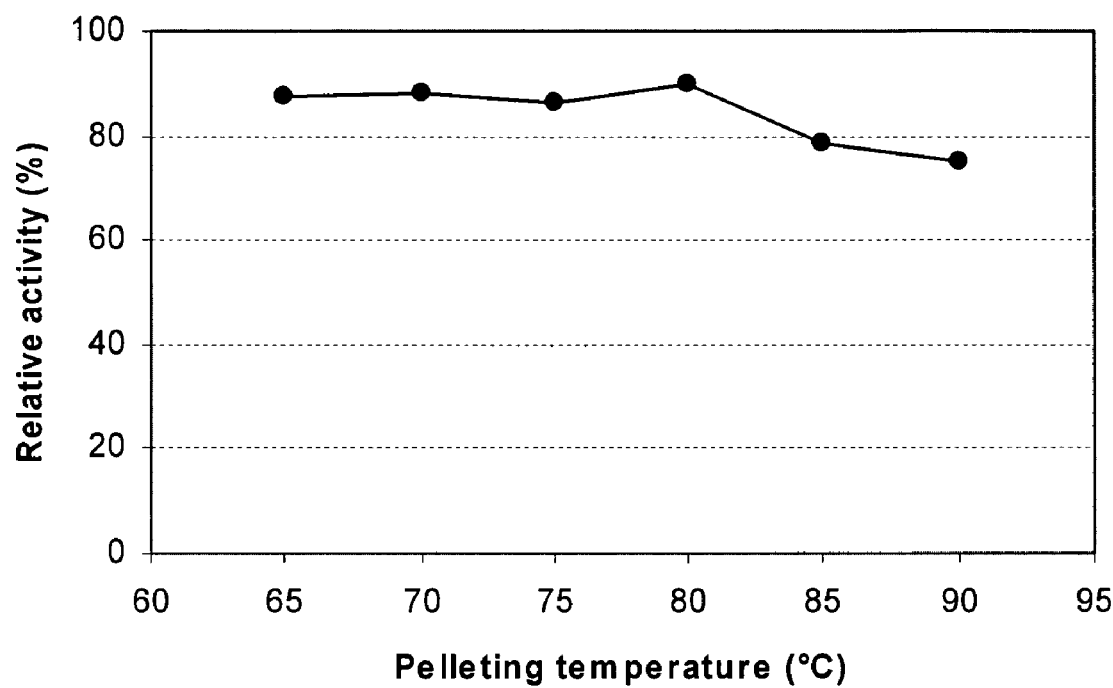
FIG. 8 shows the Influence of the pelleting temperature on cellulase activity recovery of feeds supplemented with EG28+CtCBD cellulase.

Enzyme activity recoveries before and after pelleting are presented in Table 10. The influence of pelleting temperature on the recovery of the beta-glucanase activity has also been presented in FIGS. 7 and 8. The EG28 and EG28+CtCBD cellulases were stable up to 80° C. The EG28+CtCBD cellulase tended to be more stable than EG28 at the pelleting temperature of 90° C.

TABLE 10

Enzyme activity recoveries before (meal from horizontal mixer) and after pelleting at temperatures ranging from 65 to 90° C.

| Pelleting temperature | Beta-Glucanase activity (FBU/kg of feed) | |
|---|---|---|
| | (EG28) | (EG28 + CtCBD) |
| Meal from horizontal mixer | 239 000 ± 9 000 (100%) | 1 148 000 ± 48 000 (100%) |
| Pellet (65° C.) | 227 000 ± 16 000 (95%) | 1 007 000 ± 67 000 (88%) |
| Pellet (70° C.) | 217 000 ± 5 000 (91%) | 1 012 000 ± 54 000 (88%) |
| Pellet (75° C.) | 227 000 ± 14 000 (95%) | 993 000 ± 49 000 (86%) |
| Pellet (80° C.) | 215 000 ± 6 000 (90%) | 1 030 000 ± 87 000 (90%) |
| Pellet (85° C.) | 188 000 ± 7 000 (79%) | 904 000 ± 56 000 (79%) |
| Pellet (90° C.) | 149 000 ± 8 200 (62%) | 861 000 ± 32 000 (75%) |

List of Deposited Organisms

| Strain | Plasmid contained | Deposition authority | Deposition date | Deposition number |
|---|---|---|---|---|
| *Acremonium Thermophilum* ALKO4245 | — | CBS[1] | Sep. 20, 2004 | CBS 116240 |
| *Thermoascus Aurantiacus* ALKO4242 | — | CBS[1] | Sep. 20, 2004 | CBS 116239 |
| *Chaetomium Thermophilum* ALKO4265 | — | CBS[2] | Nov. 8, 1995 | CBS 730.95 |
| *Escherichia coli* | pALK1946 | DSMZ[3] | Apr. 7, 2006 | DSM 18159 |
| *Escherichia coli* | pALK1926 | DSMZ | May 13, 2005 | DSM 17326 |

[1]The Centralbureau Voor Schimmelcultures at Uppsalalaan 8, 3584 CT, Utrecht, The Netherlands
[2]The Centralbureau Voor Schimmelcultures at Oosterstraat 1, 3742 SK BAARN, The Netherlands
[3]Deutsche Sammlung von Mikroorganismen und Zellkulturen GmbH (DSMZ), Mascheroder Weg 1 b, D-38124 Braunschweig, Germany

REFERENCES

Altschul S. F., Gish W., Miller W., Myers E. W. and Lipman D. J. (1990) "Basic local alignment search tool," *J. Mol. Biol.* 215:403-410.

Bailey M. J. and Nevalainen K. M. H. (1981) "Induction, isolation and testing of stable *Trichoderma reesei* mutants with improved production of solubilizing cellulose," *Enz. Microbiol. Technol.* 3:153-157.

Bendtsen J. D., Nielsen H., von Heijne G. and Brunak S. (2004) "Improved prediction of signal peptides: SignalP 3.0.," *J. Mol. Biol.* 340:783-795.

Gasteiger E., Gattiker A., Hoogland C., Ivanyi I., Appel R. D., and Bairoch A. (2003) "ExPASy: The proteomics server for in-depth protein knowledge and analysis," *Nucleic Acids Res.* 31:3784-3788.

Haakana H., Miettinen-Oinonen A., Joutsjoki V., Mätntylä A., Suominen P., and Vehmaanperä J. (2004) "Cloning of cellulase genes from *Melanocarpus albomyces* and their efficient expression in *Trichoderma reesei.*" *Enz Microbiol Technol.* 34:159-167.

Henrissat B. (1991) A classification of glycosyl hydrolases based on amino acid sequence similarities. *Biochem. J.* 280:309-316.

Henrissat B. and Bairoch A. (1993) New families in the classification of glycosyl hydrolases based on amino acid sequence similarities. *Biochem. J.* 293:781-788.

Henrissat B. and Bairoch A. (1996). Updating the sequence-based classification of glycosyl hydrolases. *Biochem. J.* 316:695-696

Hong J., Tamaki H., Yamamoto K., and Kumagai H. (2003) "Cloning of a gene encoding a thermo-stabile endo-β-1, 4-glucanase from *Thermoascus aurantiacus* and its expression in yeast," *Biotech. Letters* 25:657-661.

IUPAC (International Union of Pure and Applied Chemistry) (1987) "Measurement of cellulase activities," *Pure and Appl. Chem.* 59:257-268.

Joutsjoki V. V., Torkkeli T. K. and Nevalainen K. M. H. (1993) "Transformation of *Trichoderma reesei* with the *Hormoconis resinae* glucoamylase P (gamP) gene: production of a heterologous glucoamylase by *Trichoderma reesei,*" *Curr. Genet.* 24:223-228.

Karhunen T., Mätntylä A., Nevalainen K. M. H., and Suominen P. L. (1993) "High frequency one-step gene replacement in *Trichoderma reesei.* I. Endoglucanaseloverproduction," *Mol. Gen. Genet.* 241: 515-522.

Malardier L, Daboussi M. J., Julien J., Roussel F., Scazzocchio C. and Brygoo Y. (1989) "Cloning of the nitrate reductase gene (niaD) of *Aspergillus nidulans* and its use for transformation of *Fusarium oxysporum,*" *Gene* 15:147-156.

Needleman S. and Wunsch C. (1970) "A general method applicable to the search for similarities in the amino acid sequence of two proteins," *Journal of Molecular Biology* 48, 443-453.

Nielsen H., Engelbrecht J., Brunak S. and von Heijne G. (1997) "Identification of prokaryotic and eykaryotic signal peptides and prediction of their cleavage sites," *Protein Engineering* 10:1-6.

Paloheimo M., Mäntylä A., Kallio J., and Suominen P. 2003) "High-yield production of a bacterial xylanase in the filamentous fungus *Trichoderma reesei* requires a carrier polypeptide with an intact domain structure," *Appl. Env. Microbiol.* 69:7073-7082.

Penttilä M., Nevalainen H., Räffö M., Salminen E. and Knowles J. (1987) "A versatile transformation system for the cellulolytic filamentous fungus *Trichoderma reesei*." *Gene* 61:155-164.

Raeder U. and Broda P. (1985) "Rapid preparation of DNA from filamentous fungi," *Lett. Appl. Microbiol.* 1:17-20.

Rice P., Longden I. and Bleasby A. (2000) EMBOSS: "The European Molecular Biology Open Software Suite," *Trends in Genetics* 16:276-277.

Sambrook J., Fritsch E. F. and Maniatis T. (1989) *Molecular Cloning, a Laboratory Manual*. Cold Spring Harbor Laboratory, New York, US.

Sambrook J. and Russell D. W. (2001) *Molecular Cloning, a Laboratory Manual*. Cold Spring Harbor Laboratory, New York, US.

Srisodsuk M., Reinikainen T., Penttilä M. and Teeri T. (1993) "Role of the interdomain linker peptide of *Trichoderma reesei* cellobiohydrolase I in its interaction with crystalline cellulose," *J. Biol. Chem.* October 5; 268(28): 20756-61.

Stålbrand H., Siika-Aho M., Tenkanen M. and Viikari L. (1993) *J. Biotechnol.* 29:229-242.

Ward M., Shan W., Dauberman J., Weiss G., Larenas E., Bower B., Rey M., Clarkson K. and Bott R. (1993) "Cloning, sequence and preliminary structural analysis of a small, high pI endoglucanase (EGIII) from *Trichoderma reesei*." Proceedings of the second TRICEL symposium on TRICHODERMA REESEI CELLULASES AND OTHER HYDROLASES, Espoo, Finland, 1993, ed. by P. Suominen and T. Reinikainen. Foundation for Biotechnical and Industrial Fermentation Research 8 (1993):153-158.

The invention claimed is:

1. A cellulase fusion protein comprising a first amino acid sequence of an endoglucanase core having at least 95% sequence identity to SEQ ID NO:2, or a fragment thereof having cellulase activity, and a second amino acid sequence comprising a linker and cellulose binding domain (CBD) having at least 95% sequence identity to SEQ ID NO: 15, or a fragment thereof having cellulose binding activity.

2. The fusion protein of claim 1, wherein the endoglucanase belongs to glycosyl hydrolase family 5.

3. The fusion protein of claim 1, wherein the endoglucanase core is derived from T. aurantiacus CBS 116239.

4. The fusion protein of claim 1, wherein the endoglucanase core comprises amino acids 19 to 334 of SEQ ID NO: 2.

5. The fusion protein of claim 1, wherein the linker and CBD are derived from cellobiohydrolase of Chaetomium thermophilum.

6. The fusion protein of claim 1, wherein the endoglucanase core comprises the sequence of SEQ ID NO: 2, and the linker and CBD comprises the sequence of SEQ ID NO: 15.

7. The fusion protein of claim 1, comprising the amino acid sequence of SEQ ID NO: 4, or a fragment thereof having cellulase and cellulose binding activity.

8. The fusion protein of claim 1, wherein the endoglucanase core is encoded by a gene included in E. coli DSM 17326.

9. The fusion protein of claim 1, which is encoded by a fusion gene included in E. coli DSM 18159.

10. An enzyme preparation comprising the fusion protein of claim 1.

11. A process for treating cellulosic material, wherein said process comprises contacting the cellulosic material with the fusion protein of claim 1.

12. The process of claim 11, wherein the cellulosic material is textile material, plants used in animal feed, or wood-derived pulp or secondary fiber.

13. The process of claim 11, wherein oil is extracted from plant material.

14. A process for biostoning, which process comprises the step of contacting a cellulase fusion protein of claim 1 with denim fabric or garments.

15. A process for biofinishing, which comprises the step of contacting a cellulase fusion protein of claim 1 with textile materials like fabrics or garments or yarn.

16. A detergent composition comprising the fusion protein of claim 1 and detergent auxiliaries.

17. Animal feed comprising the fusion protein of claim 1.

18. A process for treating cellulosic material, wherein said process comprises contacting the cellulosic material with the enzyme preparation of claim 10.

19. A process for biostoning, which process comprises the step of contacting an enzyme preparation of claim 10 with denim fabric or garments.

20. A process for biofinishing, which comprises the step of contacting the enzyme preparation of claim 10 with textile materials like fabrics or garments or yarn.

21. The fusion protein of claim 5, wherein the *Chaetomium thermophilum* is *C. thermophilum* CBS 730.95.

22. The fusion protein of claim 1 wherein the first amino acid sequence of an endoglucanase core has at least 98% sequence identity to SEQ ID NO:2, and wherein the second amino acid sequence comprising a linker and cellulose binding domain (CBD) has at least 98% sequence identity to SEQ ID NO: 15.

* * * * *

SEQUENCE LISTING

```
<160> NUMBER OF SEQ ID NOS: 15

<210> SEQ ID NO 1
<211> LENGTH: 1317
<212> TYPE: DNA
<213> ORGANISM: Thermoascus aurantiacus
<220> FEATURE:
<221> NAME/KEY: gene
<222> LOCATION: (1)...(1317)
<220> FEATURE:
<221> NAME/KEY: intron
<222> LOCATION: (107)...(161)
<220> FEATURE:
<221> NAME/KEY: intron
<222> LOCATION: (221)...(280)
<220> FEATURE:
<221> NAME/KEY: intron
<222> LOCATION: (434)...(492)
<220> FEATURE:
<221> NAME/KEY: intron
<222> LOCATION: (558)...(631)
<220> FEATURE:
<221> NAME/KEY: intron
<222> LOCATION: (730)...(790)

<400> SEQUENCE: 1
atgaagctcg gctctctcgt gctcgctctc agcgcagcta ggcttacact gtcggcccct        60
ctcgcagaca ggaagcagga gaccaagcgt gcgaaagtat tccaatgttc gtaacatcca       120
cgtctggctt gctggcttac tggcaactga caatggcgaa gggttcggtt caaacgagtc       180
cggtgctgaa ttcggaagcc agaaccttcc aggagtcgag gtcagcatgc ctgtactctc       240
tgcattatat taatatctca agaggcttac tctttcgcag ggaaaggatt atatatggcc       300
tgatcccaac accattgaca cattgatcag caaggggatg aacatctttc gtgtcccctt       360
tatgatggag agattggttc ccaactcaat gaccggctct ccggatccga actacctggc       420
agatctcata gcggtacatt tcaattccac catgtttgga gctgtcttcg ttgtgctgac       480
atttaatggt agactgtaaa tgcaatcacc cagaaaggtg cctacgccgt cgtcgatcct       540
cataactacg gcagatagtg aggtccccgg ttctggtatt gctgctgtat atctaagtag       600
atatgtgttt ctaacatttc cacgatttca gctacaattc tataatctcg agcccttccg       660
atttccagac cttctggaaa acggtcgcct cacagtttgc ttcgaatcca ctggtcatct       720
tcgacactag taagctgaac acccgaaatt aactgagtct gagcatgtct gacaagacga       780
```

-continued

```
tccatgaaag ataacgaata ccacgatatg gaccagacct tagtcctcaa tctcaaccag    840
gccgctatcg acggcatccg ttccgccgga gccacttccc agtacatctt tgtcgagggc    900
aattcgtgga ccggggcatg gacctggacg aacgtgaacg ataacatgaa aagcctgacc    960
gacccatctg acaagatcat atacgagatg caccagtacc tggactctga cggatccggg   1020
acatcagcga cctgcgtatc ttcgaccatc ggtcaagagc gaatcaccag cgcaacgcaa   1080
tggctcaggg ccaacgggaa gaagggcatc atcggcgagt ttgcgggcgg agccaacgac   1140
gtctgcgaga cggccatcac gggcatgctg gactacatgg cccagaacac ggacgtctgg   1200
actggcgcca tctggtgggc ggccgggccg tggtggggag actacatatt ctccatggag   1260
ccggacaatg gcatcgcgta tcagcagata cttcctattt tgactccgta tctttga      1317
```

<210> SEQ ID NO 2
<211> LENGTH: 335
<212> TYPE: PRT
<213> ORGANISM: Thermoascus aurantiacus

<400> SEQUENCE: 2

```
Met Lys Leu Gly Ser Leu Val Leu Ala Leu Ser Ala Ala Arg Leu Thr
  1               5                  10                  15

Leu Ser Ala Pro Leu Ala Asp Arg Lys Gln Glu Thr Lys Arg Ala Lys
             20                  25                  30

Val Phe Gln Trp Phe Gly Ser Asn Glu Ser Gly Ala Glu Phe Gly Ser
         35                  40                  45

Gln Asn Leu Pro Gly Val Glu Gly Lys Asp Tyr Ile Trp Pro Asp Pro
     50                  55                  60

Asn Thr Ile Asp Thr Leu Ile Ser Lys Gly Met Asn Ile Phe Arg Val
 65                  70                  75                  80

Pro Phe Met Met Glu Arg Leu Val Pro Asn Ser Met Thr Gly Ser Pro
                 85                  90                  95

Asp Pro Asn Tyr Leu Ala Asp Leu Ile Ala Thr Val Asn Ala Ile Thr
            100                 105                 110

Gln Lys Gly Ala Tyr Ala Val Val Asp Pro His Asn Tyr Gly Arg Tyr
        115                 120                 125

Tyr Asn Ser Ile Ile Ser Ser Pro Ser Asp Phe Gln Thr Phe Trp Lys
    130                 135                 140

Thr Val Ala Ser Gln Phe Ala Ser Asn Pro Leu Val Ile Phe Asp Thr
145                 150                 155                 160

Asn Asn Glu Tyr His Asp Met Asp Gln Thr Leu Val Leu Asn Leu Asn
                165                 170                 175

Gln Ala Ala Ile Asp Gly Ile Arg Ser Ala Gly Ala Thr Ser Gln Tyr
            180                 185                 190

Ile Phe Val Glu Gly Asn Ser Trp Thr Gly Ala Trp Thr Trp Thr Asn
        195                 200                 205

Val Asn Asp Asn Met Lys Ser Leu Thr Asp Pro Ser Asp Lys Ile Ile
    210                 215                 220

Tyr Glu Met His Gln Tyr Leu Asp Ser Asp Gly Ser Gly Thr Ser Ala
225                 230                 235                 240

Thr Cys Val Ser Ser Thr Ile Gly Gln Glu Arg Ile Thr Ser Ala Thr
                245                 250                 255

Gln Trp Leu Arg Ala Asn Gly Lys Lys Gly Ile Ile Gly Glu Phe Ala
            260                 265                 270

Gly Gly Ala Asn Asp Val Cys Glu Thr Ala Ile Thr Gly Met Leu Asp
        275                 280                 285
```

```
Tyr Met Ala Gln Asn Thr Asp Val Trp Thr Gly Ala Ile Trp Trp Ala
    290                 295                 300
Ala Gly Pro Trp Trp Gly Asp Tyr Ile Phe Ser Met Glu Pro Asp Asn
305                 310                 315                 320
Gly Ile Ala Tyr Gln Gln Ile Leu Pro Ile Leu Thr Pro Tyr Leu
                325                 330                 335

<210> SEQ ID NO 3
<211> LENGTH: 1621
<212> TYPE: DNA
<213> ORGANISM: Thermoascus aurantiacus
<220> FEATURE:
<221> NAME/KEY: gene
<222> LOCATION: (1)...(1621)
<220> FEATURE:
<221> NAME/KEY: intron
<222> LOCATION: (107)...(161)
<220> FEATURE:
<221> NAME/KEY: intron
<222> LOCATION: (221)...(280)
<220> FEATURE:
<221> NAME/KEY: intron
<222> LOCATION: (434)...(492)
<220> FEATURE:
<221> NAME/KEY: intron
<222> LOCATION: (558)...(631)
<220> FEATURE:
<221> NAME/KEY: intron
<222> LOCATION: (730)...(790)
<220> FEATURE:
<221> NAME/KEY: intron
<222> LOCATION: (1549)...(1612)

<400> SEQUENCE: 3
atgaagctcg gctctctcgt gctcgctctc agcgcagcta ggcttacact gtcggcccct      60
ctcgcagaca ggaagcagga gaccaagcgt gcgaaagtat tccaatgttc gtaacatcca     120
cgtctggctt gctggcttac tggcaactga caatggcgaa gggttcggtt caaacgagtc     180
cggtgctgaa ttcggaagcc agaaccttcc aggagtcgag gtcagcatgc ctgtactctc     240
tgcattatat taatatctca agaggcttac tctttcgcag ggaaaggatt atatatggcc     300
tgatcccaac accattgaca cattgatcag caaggggatg aacatctttc gtgtccctt      360 tatgatggag agattggttc ccaactcaat gaccggctct ccggatccga actacctggc     420
agatctcata gcggtacatt tcaattccac catgtttgga gctgtcttcg ttgtgctgac     480
atttaatggt agactgtaaa tgcaatcacc cagaaaggtg cctacgccgt cgtcgatcct     540
cataactacg gcagatagtg aggtccccgg ttctggtatt gctgctgtat atctaagtag     600
atatgtgttt ctaacatttc cacgatttca gctacaattc tataatctcg agcccttccg     660
atttccagac cttctggaaa acggtcgcct cacagtttgc ttcgaatcca ctggtcatct     720
tcgacactag taagctgaac acccgaaatt aactgagtct gagcatgtct acaagacga      780 tccatgaaag ataacgaata ccacgatatg gaccagacct tagtcctcaa tctcaaccag     840
gccgctatcg acggcatccg ttccgccgga gccacttccc agtacatctt tgtcgagggc     900
aattcgtgga ccggggcatg gacctggacg aacgtgaacg ataacatgaa aagcctgacc     960
gacccatctg acaagatcat atacgagatg caccagtacc tggactctga cggatccggg    1020
acatcagcga cctgcgtatc ttcgaccatc ggtcaagagc gaatcaccag cgcaacgcaa    1080
tggctcaggg ccaacgggaa gaagggcatc atcggcgagt ttgcgggcgg agccaacgac    1140
gtctgcgaga cggccatcac gggcatgctg gactacatgg cccagaacac ggacgtctgg    1200
```

-continued

```
actggcgcca tctggtgggc ggccgggccg tggtggggag actacatatt ctccatggag   1260
ccggacaatg gcatcgcgta tcagcagata cttcctattt tgactccgta cgtacctggc   1320
cttgacggca gcaaccccgg caacccgacc accaccgtcg ttcctcccgc ttctacctcc   1380
acctcccgtc cgaccagcag cactagctct cccgtttcga ccccgactgg ccagcccggc   1440
ggctgcacca cccagaagtg gggccagtgc ggcggtatcg gctacaccgg ctgcactaac   1500
tgcgttgctg gcaccacctg cactcagctc aaccctggt acagccaggt atgtttctct    1560 tccccttct agactcgctt ggatttgaca gttgctaaca tctgctcaac agtgcctgta    1620
a                                                                   1621
```

<210> SEQ ID NO 4
<211> LENGTH: 415
<212> TYPE: PRT
<213> ORGANISM: Thermoascus aurantiacus

<400> SEQUENCE: 4

```
Met Lys Leu Gly Ser Leu Val Leu Ala Leu Ser Ala Ala Arg Leu Thr
 1               5                  10                  15

Leu Ser Ala Pro Leu Ala Asp Arg Lys Gln Glu Thr Lys Arg Ala Lys
            20                  25                  30

Val Phe Gln Trp Phe Gly Ser Asn Glu Ser Gly Ala Glu Phe Gly Ser
        35                  40                  45

Gln Asn Leu Pro Gly Val Glu Gly Lys Asp Tyr Ile Trp Pro Asp Pro
    50                  55                  60

Asn Thr Ile Asp Thr Leu Ile Ser Lys Gly Met Asn Ile Phe Arg Val
65                  70                  75                  80

Pro Phe Met Met Glu Arg Leu Val Pro Asn Ser Met Thr Gly Ser Pro
                85                  90                  95

Asp Pro Asn Tyr Leu Ala Asp Leu Ile Ala Thr Val Asn Ala Ile Thr
            100                 105                 110

Gln Lys Gly Ala Tyr Ala Val Val Asp Pro His Asn Tyr Gly Arg Tyr
        115                 120                 125

Tyr Asn Ser Ile Ile Ser Ser Pro Ser Asp Phe Gln Thr Phe Trp Lys
    130                 135                 140

Thr Val Ala Ser Gln Phe Ala Ser Asn Pro Leu Val Ile Phe Asp Thr
145                 150                 155                 160

Asn Asn Glu Tyr His Asp Met Asp Gln Thr Leu Val Leu Asn Leu Asn
                165                 170                 175

Gln Ala Ala Ile Asp Gly Ile Arg Ser Ala Gly Ala Thr Ser Gln Tyr
            180                 185                 190

Ile Phe Val Glu Gly Asn Ser Trp Thr Gly Ala Trp Thr Trp Thr Asn
        195                 200                 205

Val Asn Asp Asn Met Lys Ser Leu Thr Asp Pro Ser Asp Lys Ile Ile
    210                 215                 220

Tyr Glu Met His Gln Tyr Leu Asp Ser Asp Gly Ser Gly Thr Ser Ala
225                 230                 235                 240

Thr Cys Val Ser Ser Thr Ile Gly Gln Glu Arg Ile Thr Ser Ala Thr
                245                 250                 255

Gln Trp Leu Arg Ala Asn Gly Lys Lys Gly Ile Ile Gly Glu Phe Ala
            260                 265                 270

Gly Gly Ala Asn Asp Val Cys Glu Thr Ala Ile Thr Gly Met Leu Asp
        275                 280                 285

Tyr Met Ala Gln Asn Thr Asp Val Trp Thr Gly Ala Ile Trp Trp Ala
```

```
            290                 295                 300
Ala Gly Pro Trp Trp Gly Asp Tyr Ile Phe Ser Met Glu Pro Asp Asn
305                 310                 315                 320

Gly Ile Ala Tyr Gln Gln Ile Leu Pro Ile Leu Thr Pro Tyr Val Pro
                325                 330                 335

Gly Leu Asp Gly Ser Asn Pro Gly Asn Pro Thr Thr Val Val Pro
            340                 345                 350

Pro Ala Ser Thr Ser Thr Ser Arg Pro Thr Ser Ser Thr Ser Ser Pro
                355                 360                 365

Val Ser Thr Pro Thr Gly Gln Pro Gly Gly Cys Thr Thr Gln Lys Trp
370                 375                 380

Gly Gln Cys Gly Gly Ile Gly Tyr Thr Gly Cys Thr Asn Cys Val Ala
385                 390                 395                 400

Gly Thr Thr Cys Thr Gln Leu Asn Pro Trp Tyr Ser Gln Cys Leu
                405                 410                 415

<210> SEQ ID NO 5
<211> LENGTH: 1211
<212> TYPE: DNA
<213> ORGANISM: Acremonium thermophilum
<220> FEATURE:
<221> NAME/KEY: gene
<222> LOCATION: (13)...(1206)
<220> FEATURE:
<221> NAME/KEY: intron
<222> LOCATION: (96)...(154)
<220> FEATURE:
<221> NAME/KEY: intron
<222> LOCATION: (404)...(526)
<220> FEATURE:
<221> NAME/KEY: intron
<222> LOCATION: (1134)...(1197)

<400> SEQUENCE: 5
ggactgcgca tcatgcgctc ctcacccttt ctccgcgcag ctctggctgc cgctctgcct      60
ctgagcgccc atgccctcga cggaaagtcg acgaggtatg ccaatcctcg tacctctgcc     120
ctctgtagaa acaagtgacc gactgcaaag acagatactg ggactgctgc aagccgtcct     180
gcggctgggc cggaaaggcc tcggtgaacc agcccgtctt ctcgtgctcg gccgactggc     240
agcgcatcag cgacttcaac gcgaagtcgg gctgcgacgg aggctccgcc tactcgtgcg     300
ccgaccagac gccctgggcg gtcaacgaca acttctcgta cggcttcgca gccacggcca     360
tcgccggcgg ctccgagtcc agctggtgct gcgcctgcta tgcgtgagtt ctctgcaagc     420
cgcttcccac cccgctttc tgtgcaggcc gcttcccccc tacccaccca cttccccccc      480
cccgcctctg tgatcgggca tccgagctaa gttgcgtgtc gtccagactc accttcaact     540
cgggccccgt cgcgggcaag accatggtgg tgcagtcgac cagcaccggc ggcgacctgg     600
gcagcaacca gttcgacctc gccatccccg gcggcggcgt gggcatcttc aacggctgcg     660
cctcccagtt cggcggcctc cccggcgccc agtacggcgg catcagcgac cgcagccagt     720
gctcgtcctt cccgcgccg ctccagccgg gctgccagtg gcgcttcgac tggttccaga     780
acgccgacaa ccccaccttc accttccagc gcgtgcagtg cccgtccgag ctcacgtccc     840
gcacgggctg taagcgcgac gacgacgcca gctatcccgt cttcaacccg cctagcgtcc     900
ctggccttga cggcagcaac cccggcaacc cgaccaccac cgtcgttcct cccgcttcta     960
cctccacctc ccgtccgacc agcagcacta gctctcccgt ttcgaccccg actggccagc    1020
ccggcggctg caccacccag aagtggggcc agtgcggcgg tatcggctac accggctgca    1080
```
ctaactgcgt tgctggcacc acctgcactc agctcaaccc ctggtacagc caggtatgtt    1140
tctcttcccc cttctagact cgcttggatt tgacagttgc taacatctgc tcaacagtgc    1200
ctgtaactgc a                                                          1211

<210> SEQ ID NO 6
<211> LENGTH: 315
<212> TYPE: PRT
<213> ORGANISM: Acremonium thermophilum

<400> SEQUENCE: 6

Met Arg Ser Ser Pro Phe Leu Arg Ala Ala Leu Ala Ala Ala Leu Pro
1               5                   10                  15

Leu Ser Ala His Ala Leu Asp Gly Lys Ser Thr Arg Tyr Trp Asp Cys
            20                  25                  30

Cys Lys Pro Ser Cys Gly Trp Ala Gly Lys Ala Ser Val Asn Gln Pro
        35                  40                  45

Val Phe Ser Cys Ser Ala Asp Trp Gln Arg Ile Ser Asp Phe Asn Ala
    50                  55                  60

Lys Ser Gly Cys Asp Gly Gly Ser Ala Tyr Ser Cys Ala Asp Gln Thr
65                  70                  75                  80

Pro Trp Ala Val Asn Asp Asn Phe Ser Tyr Gly Phe Ala Ala Thr Ala
                85                  90                  95

Ile Ala Gly Gly Ser Glu Ser Ser Trp Cys Cys Ala Cys Tyr Ala Leu
            100                 105                 110

Thr Phe Asn Ser Gly Pro Val Ala Gly Lys Thr Met Val Val Gln Ser
        115                 120                 125

Thr Ser Thr Gly Gly Asp Leu Gly Ser Asn Gln Phe Asp Leu Ala Ile
    130                 135                 140

Pro Gly Gly Gly Val Gly Ile Phe Asn Gly Cys Ala Ser Gln Phe Gly
145                 150                 155                 160

Gly Leu Pro Gly Ala Gln Tyr Gly Gly Ile Ser Asp Arg Ser Gln Cys
                165                 170                 175

Ser Ser Phe Pro Ala Pro Leu Gln Pro Gly Cys Gln Trp Arg Phe Asp
            180                 185                 190

Trp Phe Gln Asn Ala Asp Asn Pro Thr Phe Thr Phe Gln Arg Val Gln
        195                 200                 205

Cys Pro Ser Glu Leu Thr Ser Arg Thr Gly Cys Lys Arg Asp Asp Asp
    210                 215                 220

Ala Ser Tyr Pro Val Phe Asn Pro Pro Ser Val Pro Gly Leu Asp Gly
225                 230                 235                 240

Ser Asn Pro Gly Asn Pro Thr Thr Thr Val Val Pro Pro Ala Ser Thr
                245                 250                 255

Ser Thr Ser Arg Pro Thr Ser Ser Thr Ser Ser Pro Val Ser Thr Pro
            260                 265                 270

Thr Gly Gln Pro Gly Gly Cys Thr Thr Gln Lys Trp Gly Gln Cys Gly
        275                 280                 285

Gly Ile Gly Tyr Thr Gly Cys Thr Asn Cys Val Ala Gly Thr Thr Cys
    290                 295                 300

Thr Gln Leu Asn Pro Trp Tyr Ser Gln Cys Leu
305                 310                 315

<210> SEQ ID NO 7
<211> LENGTH: 1663
<212> TYPE: DNA
<213> ORGANISM: Chaetomium thermophilum

```
<220> FEATURE:
<221> NAME/KEY: gene
<222> LOCATION: (1)...(1663)
<220> FEATURE:
<221> NAME/KEY: intron
<222> LOCATION: (1591)...(1654)

<400> SEQUENCE: 7
atgatgtata agaagttcgc cgctctcgcc gccctcgtgg ctggcgcctc cgcccagcag      60
gcttgctccc tcaccgctga gaaccaccct agcctcacct ggaagcgctg cacctctggc     120
ggcagctgct cgaccgtgaa cggcgccgtc accatcgatg ccaactggcg ctggactcac     180
accgtctccg gctcgaccaa ctgctacacc ggcaaccagt gggatacctc cctctgcact     240
gatggcaaga gctgcgccca gacctgctgc gtcgatggcg ctgactactc ttcgacctat     300
ggtatcacca ccagcggtga ctccctgaac ctcaagttcg tcaccaagca ccagtacggc     360
accaacgtcg gctcccgtgt ctatctgatg gagaacgaca ccaagtacca gatgttcgag     420
ctcctcggca acgagttcac cttcgatgtc gatgtctcca acctgggctg cggtctcaac     480
ggcgccctct acttcgtttc catggatgct gatggtggca tgagcaaata ctctggcaac     540
aaggctggcg ccaagtacgg taccggctac tgcgatgctc agtgcccgcg cgacctcaag     600
ttcatcaacg gcgaggccaa cgttgggaac tggaccccct cgaccaacga tgccaacgcc     660
ggcttcggcc gctatggcag ctgctgctct gagatggatg tctgggaggc caacaacatg     720
gctactgcct tcactcctca cccttgcacc accgttggcc agagccgctg cgaggccgac     780
acctgcggtg gcacctacag ctctgaccgc tatgctggtg tttgcgaccc tgatggctgc     840
gacttcaacg cctaccgcca aggcgacaag accttctacg gcaagggcat gactgtcgac     900
accaacaaga agatgaccgt cgtcacccag ttccacaaga actcggctgg cgtcctcagc     960
gagatcaagc gcttctacgt ccaggacggc aagatcattg ccaacgctga gtccaagatc    1020
cccggcaacc ccggaaactc cattacccag gagtattgcg atgcccagaa ggtcgccttc    1080
agtaacaccg atgacttcaa ccgcaagggc ggtatggctc agatgagcaa ggccctcgca    1140
ggccccatgg tcctggtcat gtccgtctgg gatgaccact acgccaacat gctctggctc    1200
gactcgacct accccatcga ccaggccggc gccccggcg ccgagcgcgg tgcttgcccg    1260
accacctccg gtgtccctgc cgagatcgag gcccaggtcc caacagcaa cgtcatcttc    1320 tccaacatcc gtttcggccc catcggctcg accgtccctg ccttgacgg cagcaacccc    1380 ggcaacccga ccaccaccgt cgttcctccc gcttctacct ccacctcccg tccgaccagc    1440
agcactagct ctcccgtttc gaccccgact ggccagcccg gcggctgcac cacccagaag    1500
tggggccagt gcggcggtat cggctacacc ggctgcacta actgcgttgc tggcaccacc    1560
tgcactcagc tcaacccctg gtacagccag gtatgtttct cttccccctt ctagactcgc    1620
ttggatttga cagttgctaa catctgctca acagtgcctg taa                       1663

<210> SEQ ID NO 8
<211> LENGTH: 1076
<212> TYPE: DNA
<213> ORGANISM: Acremonium thermophilum
<220> FEATURE:
<221> NAME/KEY: gene
<222> LOCATION: (1)...(1076)
<220> FEATURE:
<221> NAME/KEY: intron
<222> LOCATION: (84)...(142)
<220> FEATURE:
<221> NAME/KEY: intron
<222> LOCATION: (392)...(514)
```

<400> SEQUENCE: 8

```
atgcgctcct cacccttct ccgcgcagct ctggctgccg ctctgcctct gagcgcccat      60
gccctcgacg gaaagtcgac gaggtatgcc aatcctcgta cctctgccct ctgtagaaac     120
aagtgaccga ctgcaaagac agatactggg actgctgcaa gccgtcctgc ggctggccgg     180
gaaaggcctc ggtgaaccag cccgtcttct cgtgctcggc cgactggcag cgcatcagcg     240
acttcaacgc gaagtcgggc tgcgacggag gctccgccta ctcgtgcgcc gaccagacgc     300
cctgggcggt caacgacaac ttctcgtacg gcttcgcagc cacggccatc gccggcggct     360
ccgagtccag ctggtgctgc gcctgctatg cgtgagttct ctgcaagccg cttcccaccc     420
ccgctttctg tgcaggccgc ttcccccta cccacccact tccccccccc cgcctctgtg      480
atcgggcatc cgagctaagt tgcgtgtcgt ccagactcac cttcaactcg gccccgtcg      540
cgggcaagac catggtggtg cagtcgacca gcaccggcgg cgacctgggc agcaaccagt     600
tcgacctcgc catccccggc ggcggcgtgg gcatcttcaa cggctgcgcc tcccagttcg     660
gcggcctccc cggcgcccag tacgcggca tcagcgaccg cagccagtgc tcgtccttcc      720
ccgcgccgct ccagccgggc tgccagtggc gcttcgactg gttccagaac gccgacaacc     780
ccaccttcac cttccagcgc gtgcagtgcc cgtccgagct cacgtccgc acgggctgta      840
agcgcgacga cgacgccagc tatcccgtct tcaacccgcc tagcggtggc tcccccagca     900
ccaccagcac caccaccagc tccccgtccg gtcccacggg caaccctcct ggaggcggtg     960
gctgcactgc ccagaagtgg gcccagtgcg gcggcactgg cttcacgggc tgcaccacct    1020
gcgtctcggg caccacctgc caggtgcaga accagtggta ttcccagtgt ctgtga         1076
```

<210> SEQ ID NO 9  
<211> LENGTH: 45  
<212> TYPE: DNA  
<213> ORGANISM: Thermoascus aurantiacus

<400> SEQUENCE: 9

```
attaaccgcg gactgcgcat catgaagctc ggctctctcg tgctc                       45
```

<210> SEQ ID NO 10  
<211> LENGTH: 29  
<212> TYPE: DNA  
<213> ORGANISM: Thermoascus aurantiacus

<400> SEQUENCE: 10

```
aactgaggca tagaaactga cgtcatatt                                         29
```

<210> SEQ ID NO 11  
<211> LENGTH: 28  
<212> TYPE: DNA  
<213> ORGANISM: Chaetomium thermophilum

<400> SEQUENCE: 11

```
taatttacgt acctggcctt gacggcag                                          28
```

<210> SEQ ID NO 12  
<211> LENGTH: 30  
<212> TYPE: DNA  
<213> ORGANISM: Chaetomium thermophilum

<400> SEQUENCE: 12

```
attaactgca gttacaggca ctgttgagca                                        30
```

-continued

```
<210> SEQ ID NO 13
<211> LENGTH: 42
<212> TYPE: DNA
<213> ORGANISM: Acremonium thermophilum

<400> SEQUENCE: 13
attaaccgcg gactgcgcat catgcgctcc tcacccttc tc                          42

<210> SEQ ID NO 14
<211> LENGTH: 33
<212> TYPE: DNA
<213> ORGANISM: Acremonium thermophilum

<400> SEQUENCE: 14
ttaatctgca gtcacagaca ctgggaatac cac                                    33

<210> SEQ ID NO 15
<211> LENGTH: 81
<212> TYPE: PRT
<213> ORGANISM: Chaetomium thermophilum

<400> SEQUENCE: 15

Val Pro Gly Leu Asp Gly Ser Asn Pro Gly Asn Pro Thr Thr Thr Val
 1               5                  10                  15

Val Pro Pro Ala Ser Thr Ser Thr Ser Arg Pro Thr Ser Ser Thr Ser
             20                  25                  30

Ser Pro Val Ser Thr Pro Thr Gly Gln Pro Gly Gly Cys Thr Thr Gln
         35                  40                  45

Lys Trp Gly Gln Cys Gly Gly Ile Gly Tyr Thr Gly Cys Thr Asn Cys
     50                  55                  60

Val Ala Gly Thr Thr Cys Thr Gln Leu Asn Pro Trp Tyr Ser Gln Cys
 65                  70                  75                  80

Leu
```